(12) United States Patent
Wisniewski et al.

(10) Patent No.: US 10,010,272 B2
(45) Date of Patent: Jul. 3, 2018

(54) TISSUE-INTEGRATING ELECTRONIC APPARATUS

(71) Applicant: PROFUSA, Inc., South San Francisco, CA (US)

(72) Inventors: Natalie A. Wisniewski, San Francisco, CA (US); Kurt E. Petersen, Milpitas, CA (US); Kristen Helton, Seattle, WA (US); William A. McMillan, La Honda, CA (US)

(73) Assignee: Profusa, Inc., South San Francisco, CA (US)

( * ) Notice: Subject to any disclaimer, the term of this patent is extended or adjusted under 35 U.S.C. 154(b) by 349 days.

(21) Appl. No.: 14/461,144

(22) Filed: Aug. 15, 2014

(65) Prior Publication Data

US 2014/0357964 A1 Dec. 4, 2014

Related U.S. Application Data

(63) Continuation-in-part of application No. 12/789,048, filed on May 27, 2010, now Pat. No. 9,517,023, and a continuation of application No. 13/267,741, filed on Oct. 6, 2011.

(60) Provisional application No. 61/390,252, filed on Oct. 6, 2010.

(51) Int. Cl.
*A61B 5/1455* (2006.01)
*A61B 5/145* (2006.01)
*A61B 5/1486* (2006.01)
*A61B 5/00* (2006.01)
*A61B 5/01* (2006.01)
*A61B 5/11* (2006.01)
*A61B 5/0215* (2006.01)

(52) U.S. Cl.
CPC ........ *A61B 5/1451* (2013.01); *A61B 5/14865* (2013.01); *A61B 5/742* (2013.01); *A61B 5/0031* (2013.01); *A61B 5/0084* (2013.01); *A61B 5/01* (2013.01); *A61B 5/0215* (2013.01); *A61B 5/11* (2013.01)

(58) Field of Classification Search
None
See application file for complete search history.

(56) References Cited

U.S. PATENT DOCUMENTS

| | | | |
|---|---|---|---|
| 4,703,756 A | 11/1987 | Gough et al. |
| 5,001,054 A | 3/1991 | Wagner |
| 5,161,532 A | 11/1992 | Joseph |
| 5,284,140 A | 2/1994 | Allen et al. |
| 5,342,789 A | 8/1994 | Chick et al. |
| 5,512,246 A | 4/1996 | Russell et al. |

(Continued)

FOREIGN PATENT DOCUMENTS

| | | |
|---|---|---|
| CN | 1675547 A | 9/2005 |
| CN | 1882278 A | 12/2006 |

(Continued)

OTHER PUBLICATIONS

Examination Report for Australian Application No. 2011311889, dated Dec. 20, 2013.

(Continued)

*Primary Examiner* — Eric Winakur
*Assistant Examiner* — Marjan Fardanesh

(57) ABSTRACT

Tissue-integrating electronic apparatuses, systems comprising such apparatuses and methods of using these apparatuses and systems for the detection of one or more signals are provided.

32 Claims, 18 Drawing Sheets

(56) References Cited

U.S. PATENT DOCUMENTS

| | | |
|---|---|---|
| 5,551,422 A | 9/1996 | Simonsen et al. |
| 5,777,060 A | 7/1998 | Van Antwerp |
| 5,895,658 A | 4/1999 | Fossel |
| 6,002,954 A | 12/1999 | Van Antwerp et al. |
| 6,011,984 A | 1/2000 | Van Antwerp et al. |
| 6,013,122 A | 1/2000 | Klitzman et al. |
| 6,040,194 A | 3/2000 | Chick et al. |
| 6,175,752 B1 | 1/2001 | Say et al. |
| 6,212,416 B1 | 4/2001 | Ward et al. |
| 6,299,604 B1 | 10/2001 | Ragheb et al. |
| 6,319,540 B1 | 11/2001 | Van Antwerp et al. |
| 6,376,971 B1 | 4/2002 | Pelrine et al. |
| 6,379,622 B1 | 4/2002 | Polak et al. |
| 6,475,750 B1 | 11/2002 | Han et al. |
| 6,485,703 B1 | 11/2002 | Cote et al. |
| 6,497,729 B1 | 12/2002 | Moussy et al. |
| 6,543,110 B1 | 4/2003 | Pelrine et al. |
| 6,565,509 B1 | 5/2003 | Say et al. |
| 6,565,960 B2 | 5/2003 | Koob et al. |
| 6,583,533 B2 | 6/2003 | Pelrine et al. |
| 6,602,678 B2 | 8/2003 | Kwon et al. |
| 6,642,015 B2 | 11/2003 | Vachon et al. |
| 6,671,527 B2 | 12/2003 | Petersson et al. |
| 6,702,857 B2 | 3/2004 | Brauker et al. |
| 6,750,311 B1 | 6/2004 | Van Antwerp et al. |
| 6,766,183 B2 | 7/2004 | Walsh et al. |
| 6,794,195 B2 | 9/2004 | Colvin, Jr. |
| 6,804,544 B2 | 10/2004 | Van Antwerp et al. |
| 6,818,226 B2 | 11/2004 | Reed et al. |
| 6,821,530 B2 | 11/2004 | Koob et al. |
| 6,844,023 B2 | 1/2005 | Schulman et al. |
| 6,858,184 B2 | 2/2005 | Pelrine et al. |
| 6,916,660 B2 | 7/2005 | Wang et al. |
| 6,927,246 B2 | 8/2005 | Noronha et al. |
| 6,965,791 B1 | 11/2005 | Hitchcock et al. |
| 6,994,691 B2 | 2/2006 | Ejlersen |
| 7,045,361 B2 | 5/2006 | Heiss et al. |
| 7,060,503 B2 | 6/2006 | Colvin, Jr. |
| 7,067,194 B2 | 6/2006 | Mao et al. |
| 7,110,803 B2 | 9/2006 | Shults et al. |
| 7,132,049 B2 | 11/2006 | Hou et al. |
| 7,134,999 B2 | 11/2006 | Brauker et al. |
| 7,153,265 B2 | 12/2006 | Vachon |
| 7,162,289 B2 | 1/2007 | Shah et al. |
| 7,186,789 B2 | 3/2007 | Hossainy et al. |
| 7,192,450 B2 | 3/2007 | Brauker et al. |
| 7,202,947 B2 | 4/2007 | Liu et al. |
| 7,226,978 B2 | 6/2007 | Tapsak et al. |
| 7,228,159 B2 | 6/2007 | Petersson et al. |
| 7,406,345 B2 | 7/2008 | Muller et al. |
| 7,424,317 B2 | 9/2008 | Parker et al. |
| 7,450,980 B2 | 11/2008 | Kawanishi |
| 7,468,575 B2 | 12/2008 | Pelrine et al. |
| 7,521,019 B2 | 4/2009 | Polak et al. |
| 7,541,598 B2 | 6/2009 | Aasmul |
| 7,567,347 B2 | 7/2009 | Aasmul |
| 7,629,172 B2 | 12/2009 | Alarcon et al. |
| 7,653,424 B2 | 1/2010 | March |
| 7,704,704 B2 | 4/2010 | Ibey et al. |
| 7,772,286 B2 | 8/2010 | Muller et al. |
| 7,869,853 B1 | 1/2011 | Say et al. |
| 7,923,064 B2 | 4/2011 | Pelrine et al. |
| 7,927,519 B2 | 4/2011 | Domschke et al. |
| 7,939,332 B2 | 5/2011 | Colvin, Jr. |
| 7,972,628 B2 | 7/2011 | Ratner et al. |
| 8,008,088 B2 | 8/2011 | Bellott et al. |
| 8,057,041 B2 | 11/2011 | Muller et al. |
| 8,088,595 B2 | 1/2012 | Ibey et al. |
| 8,131,333 B2 | 3/2012 | Chapoy et al. |
| 8,206,622 B2 | 6/2012 | Kammermeier et al. |
| 8,318,193 B2 | 11/2012 | Ratner et al. |
| 8,346,337 B2 | 1/2013 | Heller et al. |
| 8,346,363 B2 | 1/2013 | Darvish et al. |
| 8,368,556 B2 | 2/2013 | Sicurello et al. |
| 8,372,423 B2 | 2/2013 | Marshall et al. |
| 8,372,630 B2 | 2/2013 | Uematsu et al. |
| 8,382,700 B2 | 2/2013 | Straessler et al. |
| 8,385,998 B2 | 2/2013 | Zhang et al. |
| 8,394,463 B1 | 3/2013 | Chiu et al. |
| 8,423,114 B2 | 4/2013 | Simpson et al. |
| 8,452,361 B2 | 5/2013 | Muller |
| 8,452,363 B2 | 5/2013 | Muller et al. |
| 8,460,231 B2 | 6/2013 | Brauker et al. |
| 8,465,425 B2 | 6/2013 | Heller et al. |
| 8,483,793 B2 | 7/2013 | Simpson et al. |
| 8,508,109 B2 | 8/2013 | Pelrine et al. |
| 8,512,245 B2 | 8/2013 | Markle et al. |
| 8,527,025 B1 | 9/2013 | Shults et al. |
| 8,527,026 B2 | 9/2013 | Shults et al. |
| 8,535,262 B2 | 9/2013 | Markle et al. |
| 8,543,182 B2 | 9/2013 | Botvinick et al. |
| 8,543,184 B2 | 9/2013 | Boock et al. |
| 8,543,354 B2 | 9/2013 | Luo et al. |
| 8,579,879 B2 | 11/2013 | Palerm et al. |
| 8,608,924 B2 | 12/2013 | Cooper et al. |
| RE44,695 E | 1/2014 | Simpson et al. |
| 8,622,903 B2 | 1/2014 | Jin et al. |
| 8,623,639 B2 | 1/2014 | Amiss et al. |
| 8,628,471 B2 | 1/2014 | Mazar et al. |
| 8,647,271 B2 | 2/2014 | Muller et al. |
| 8,647,393 B2 | 2/2014 | Marshall et al. |
| 8,666,471 B2 | 3/2014 | Rogers et al. |
| 8,927,022 B2 | 1/2015 | Maginness et al. |
| 8,940,544 B2 | 1/2015 | Suri et al. |
| 8,945,942 B2 | 2/2015 | Herbrechtsmeier et al. |
| 9,244,064 B2 | 1/2016 | Muller et al. |
| 9,826,926 B2 | 11/2017 | Muller et al. |
| 2002/0043651 A1 | 4/2002 | Darrow et al. |
| 2002/0048577 A1 | 4/2002 | Bornstein et al. |
| 2002/0050769 A1 | 5/2002 | Pelrine et al. |
| 2002/0094526 A1 | 7/2002 | Bayley et al. |
| 2002/0106314 A1 | 8/2002 | Pelrine et al. |
| 2002/0193672 A1 | 12/2002 | Walsh et al. |
| 2003/0004554 A1 | 1/2003 | Riff et al. |
| 2003/0050542 A1 | 3/2003 | Reihl et al. |
| 2003/0088682 A1 | 5/2003 | Hlasny |
| 2003/0099682 A1 | 5/2003 | Moussy et al. |
| 2003/0153026 A1 | 8/2003 | Alarcon et al. |
| 2003/0171666 A1 | 9/2003 | Loeb et al. |
| 2003/0208166 A1 | 11/2003 | Schwartz |
| 2004/0106951 A1 | 6/2004 | Edman et al. |
| 2004/0143221 A1 | 7/2004 | Shadduck |
| 2004/0161853 A1 | 8/2004 | Yang et al. |
| 2004/0176669 A1 | 9/2004 | Colvin, Jr. |
| 2004/0195528 A1 | 10/2004 | Reece et al. |
| 2004/0234962 A1 | 11/2004 | Alarcon et al. |
| 2004/0258732 A1 | 12/2004 | Shikinami |
| 2004/0259270 A1 | 12/2004 | Wolf |
| 2005/0027175 A1 | 2/2005 | Yang |
| 2005/0095174 A1 | 5/2005 | Wolf |
| 2005/0096587 A1 | 5/2005 | Santini, Jr. et al. |
| 2005/0118726 A1 | 6/2005 | Schultz et al. |
| 2005/0119737 A1 | 6/2005 | Bene et al. |
| 2005/0154374 A1 | 7/2005 | Hunter et al. |
| 2005/0182389 A1 | 8/2005 | LaPorte et al. |
| 2005/0237518 A1 | 10/2005 | Colvin, Jr. et al. |
| 2005/0245799 A1 | 11/2005 | Brauker et al. |
| 2006/0002890 A1 | 1/2006 | Hersel et al. |
| 2006/0002969 A1 | 1/2006 | Kyriakides et al. |
| 2006/0089548 A1 | 4/2006 | Hogan |
| 2006/0148983 A1 | 7/2006 | Muller et al. |
| 2006/0155179 A1 | 7/2006 | Muller et al. |
| 2006/0252976 A1 | 11/2006 | Rosero |
| 2006/0270919 A1 | 11/2006 | Brenner |
| 2006/0275340 A1 | 12/2006 | Udipi et al. |
| 2006/0289307 A1 | 12/2006 | Yu et al. |
| 2007/0002470 A1 | 1/2007 | Domschke et al. |
| 2007/0004046 A1 | 1/2007 | Abbott |
| 2007/0010702 A1 | 1/2007 | Wang et al. |
| 2007/0030443 A1 | 2/2007 | Chapoy et al. |
| 2007/0093617 A1 | 4/2007 | DesNoyer et al. |
| 2007/0105176 A1 | 5/2007 | Ibey et al. |
| 2007/0134290 A1 | 6/2007 | Rowland et al. |
| 2007/0135698 A1 | 6/2007 | Shah et al. |

(56) References Cited

U.S. PATENT DOCUMENTS

| | | |
|---|---|---|
| 2007/0244379 A1 | 10/2007 | Boock et al. |
| 2007/0270675 A1 | 11/2007 | Kane et al. |
| 2008/0020012 A1 | 1/2008 | Ju et al. |
| 2008/0136052 A1 | 6/2008 | Pelrine et al. |
| 2008/0139903 A1 | 6/2008 | Bruce et al. |
| 2008/0191585 A1 | 8/2008 | Pelrine et al. |
| 2008/0249381 A1 | 10/2008 | Muller et al. |
| 2009/0005663 A1 | 1/2009 | Parker et al. |
| 2009/0131773 A1 | 5/2009 | Struve et al. |
| 2009/0187084 A1 | 7/2009 | Kristensen et al. |
| 2009/0221891 A1 | 9/2009 | Yu et al. |
| 2009/0270953 A1 | 10/2009 | Ecker et al. |
| 2010/0113901 A1 | 5/2010 | Zhang et al. |
| 2010/0123121 A1 | 5/2010 | Taylor |
| 2010/0160749 A1 | 6/2010 | Gross et al. |
| 2010/0185066 A1 | 7/2010 | March |
| 2010/0222657 A1 | 9/2010 | Ibey et al. |
| 2010/0249548 A1 | 9/2010 | Mueller |
| 2010/0303772 A1 | 12/2010 | McMillan et al. |
| 2010/0305413 A1 | 12/2010 | Paterson |
| 2011/0028806 A1 | 2/2011 | Merritt et al. |
| 2011/0036994 A1 | 2/2011 | Frayling |
| 2011/0154641 A1 | 6/2011 | Pelrine et al. |
| 2011/0155307 A1 | 6/2011 | Pelrine et al. |
| 2011/0224514 A1 | 9/2011 | Muller et al. |
| 2011/0230835 A1 | 9/2011 | Muller et al. |
| 2012/0123276 A1 | 5/2012 | Govari et al. |
| 2012/0140094 A1 | 6/2012 | Shpunt et al. |
| 2012/0172692 A1 | 7/2012 | Tamada et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0245445 A1 | 9/2012 | Black et al. |
| 2012/0258551 A1 | 10/2012 | Herbrechtsmeier et al. |
| 2012/0265034 A1 | 10/2012 | Wisniewski et al. |
| 2012/0283538 A1 | 11/2012 | Rose et al. |
| 2012/0296311 A1 | 11/2012 | Brauker et al. |
| 2013/0006069 A1 | 1/2013 | Gil et al. |
| 2013/0022648 A1 | 1/2013 | Maginness et al. |
| 2013/0030273 A1 | 1/2013 | Tapsak et al. |
| 2013/0060105 A1 | 3/2013 | Shah et al. |
| 2013/0158413 A1 | 6/2013 | Lisogurski et al. |
| 2013/0172699 A1 | 7/2013 | Rebec et al. |
| 2013/0211213 A1 | 8/2013 | Dehennis et al. |
| 2013/0213110 A1 | 8/2013 | Papadimitrakopoulos et al. |
| 2013/0213112 A1 | 8/2013 | Stumber |
| 2013/0229660 A1 | 9/2013 | Goldschmidt et al. |
| 2013/0231542 A1 | 9/2013 | Simpson et al. |
| 2013/0302908 A1 | 11/2013 | Amiss et al. |
| 2013/0310666 A1 | 11/2013 | Shults et al. |
| 2013/0310670 A1 | 11/2013 | Boock et al. |
| 2013/0311103 A1 | 11/2013 | Cooper et al. |
| 2013/0313130 A1 | 11/2013 | Little et al. |
| 2013/0337468 A1 | 12/2013 | Muller et al. |
| 2014/0000338 A1 | 1/2014 | Luo et al. |
| 2014/0148596 A1 | 5/2014 | Dichtel et al. |
| 2014/0275869 A1 | 9/2014 | Kintz et al. |
| 2014/0316224 A1 | 10/2014 | Sato |
| 2014/0364707 A1 | 12/2014 | Kintz et al. |
| 2016/0213288 A1 | 7/2016 | Wisniewski et al. |
| 2016/0374556 A1 | 12/2016 | Colvin et al. |
| 2017/0087376 A1 | 3/2017 | McMillan et al. |
| 2017/0325722 A1 | 11/2017 | Wisniewski et al. |

FOREIGN PATENT DOCUMENTS

| | | |
|---|---|---|
| EP | 2517619 B1 | 5/2013 |
| JP | 2004-537344 | 12/2004 |
| JP | 2008/541881 | 11/2008 |
| WO | WO 91/09312 | 6/1991 |
| WO | WO 97/19188 | 5/1997 |
| WO | WO 98/06406 | 2/1998 |
| WO | WO 00/02048 | 1/2000 |
| WO | WO 2001/006579 | 1/2001 |
| WO | WO 2001/018543 | 3/2001 |
| WO | WO 2002/087610 | 11/2002 |
| WO | WO 2005/059037 | 6/2005 |
| WO | WO 2005/120631 | 12/2005 |
| WO | WO 2006/004595 | 1/2006 |
| WO | WO 2006/044972 | 4/2006 |
| WO | WO 2006/065266 | 6/2006 |
| WO | WO 2006/130461 | 12/2006 |
| WO | WO 2007/065653 | 6/2007 |
| WO | WO 2007/126444 | 11/2007 |
| WO | WO 2008/141241 | 11/2008 |
| WO | WO 2008/143651 | 11/2008 |
| WO | WO 2009/019470 | 2/2009 |
| WO | WO 2009/087373 | 7/2009 |
| WO | WO 2009/106805 | 9/2009 |
| WO | WO 2010/116142 | 10/2010 |
| WO | WO 2010/133831 | 11/2010 |
| WO | WO 2010/141377 | 12/2010 |
| WO | WO 2011/101624 | 8/2011 |
| WO | WO 2011/101625 | 8/2011 |
| WO | WO 2011/101626 | 8/2011 |
| WO | WO 2011/101627 | 8/2011 |
| WO | WO 2011/101628 | 8/2011 |
| WO | WO 2013/132400 | 9/2013 |
| WO | WO 2014/158988 | 10/2014 |
| WO | WO 2014/160258 | 10/2014 |
| WO | WO 2014/197786 | 12/2014 |

OTHER PUBLICATIONS

Examination Report for Australian Application No. 2011311889, dated May 28, 2014.

Office Action for Chinese Application No. 201180057627.5, dated Dec. 15, 2014.

Notice of Reasons for Rejection for Japanese Application No. 2013-532954, dated Mar. 31, 2015.

International Search Report and Written Opinion for International Application No. PCT/US2011/055157, dated Jan. 23, 2012.

Office Action for U.S. Appl. No. 13/267,741, dated Mar. 20, 2015.

Office Action for U.S. Appl. No. 13/267,741, dated Apr. 1, 2014.

Office Action for U.S. Appl. No. 13/267,741, dated Oct. 7, 2015.

Office Action for U.S. Appl. No. 13/267,741, dated Nov. 20, 2014.

Examination Repot for Australian Application No. 2010256930, dated Dec. 18, 2013.

English Translation of Office Action for Korean Patent Application No. 10-2013-7010584, dated Mar. 16, 2016.

Alexeev et al., "Protonic crystal glucose-sensing material for non-invasive monitoring of glucose in tear fluid," Clinical Chemistry, 50(12):2353-2360 (2004).

Aslan et al., "Nanogold plasmon-resonance-based glucose sensing 2: wavelengthratiometric resonance light scattering," Anal. Chem., 77(7):2007-2014 (2005).

Badylak et al., "Immune response to biologic scaffold materials," Seminars in Immunology, 20(2):109-116 (2008).

Ballerstadt et al., "Competitive-binding assay method based on fluorescence quenching of ligands held in close proximity by a multivalent receptor," Anal. Chem., Acta. 345:203-212 (1997).

Bhardwaj, U. et al. "A review of the development of a vehicle for localized and controlled drug delivery for implantable biosensors," Journal of Diabetes Science and Technology, 2(6):1016-1029 (2008).

Billingsley et al., "Fluorescent nano-optodes for glucose detection," Anal. Chem., 82(9):3707-3713 (2010).

Brasuel et al., "Fluorescent nanosensors for intracellular chemical analysis: decyl methacrylate liquid polymer matrix and ion-exchange-based potassium pebble sensors with real-time application to viable rat C6 glioma cells," Anal. Chem., 73(10):2221-2228 (2001).

Brasuel et al., "Liquid polymer nano-pebbles for CL-analysis and biological applications," Analyst, 128(10):1262-1267 (2003).

(56) References Cited

OTHER PUBLICATIONS

Braun et al., "Comparison of tumor and normal tissue oxygen tension measurements using oxylite or microelectrodes in rodents," Am. J. Physiol. Heart Circ. Physiol., 280(6):H2533-H2544 (2001).
Bridges et al., "Chronic inflammatory responses to microgel-based implant coatings," J Biomed. Mater. Res. A., 94(1):252-258 (2010).
Chaudhary et al., "Evaluation of glucose sensitive affinity binding assay entrapped in fluorescent dissolved-core alginate microspheres," Biotechnology and Bioengineering, 104(6):1075-1085 (2009).
Cordiero, P.G. et al., "The protective effect of L-arginine on ischemia-reperfusion injury in rat skin flaps," Plast Reconstruct Surg., 100(5):1227-1233 (1997).
Dunphy, I. et al., "Oxyphor R2 and G2: phosphors for measuring oxygen by oxygen-dependent quenching phosphorescence," Anal. Biochem., 310:191-198 (2002).
Garg, S.K. et al., "Improved glucose excursions using an implantable real-time continuous glucose sensor in adults with Type 1 diabetes," Diabetes Care, 27(3): 734-738 (2004).
Henninger, N., et al., "Tissue response to subcutaneous implantation of glucose-oxidase-based glucose sensors in rats," Biosens Bioelectron, 23(1):26-34 (2007).
Horgan et al., "Crosslinking of phenylboronic acid receptors as a means of glucose selective holographic detection," Biosensors and Bioelectronics, 21(9):1838-1845 (2006).
Ibey et al., "Competitive binding assay for glucose based on glycodendrimer fluorophore conjugates," Anal. Chem., 77(21):7039-7046 (2005).
Isenhath et al., "A mouse model to evaluate the interface between skin and a percutaneous device," J Biomed. Mater. Research, 83A:915-922 (2007).
Ju, Y. M. et al., "A novel porous collagen scaffold around an implantable biosensor for improving biocompatibility. I. In vitrol in vivo stability of the scaffold and in vitro sensitivity of the glucose sensor with scaffold," J Biomed. Mater. Research, 87A:136-146 (2008), Available online Dec. 17, 2007.
Kaehr et al., "Multiphoton fabrication of chemically responsive protein hydrogels for microactuation," PNAS USA, 105(26):8850-8854 (2008).
Kasprzak, S. E., "Small-scale polymer structures enabled by thiol-ene copolymer systems," Doctoral Dissertation, Georgia Institute of Technology, May 2009.
Klimowicz, A. et al., "Evaluation of skin penetration of topically applied drugs by cutaneous microdialysis:acyclovir vs salicylic acid," J Clin Pharm Ther 3(2):143-148 (2007).
Kloxin, A. M. et al., "Photodegradable hydrogels for dynamic tuning of physical and chemical properties," Science, 324:59-63 (2009).
Mansouri et al., "A minature optical glucose sensor based on affinity binding," Nature Biotechnology, 23:885-890 (1984).
Marshall et al., "Biomaterials with tightly controlled pore size that promote vascular in-growth," ACS Polymer Preprints, 45(2):100-101 (2004).
McShane et al., "Glucose monitoring using implanted fluorescent microspheres," IEEE Engineering in Medicine and Biology Magazine, 19(6):36-45 (2000).
Nagler, A. et al., "Topical treatment of cutaneous chronic graft versus host disease with halofuginone: a novel inhibitor of collagen Type 1 Synthesis," Transplantation, 68(11):1806-1809 (1999).
Nielsen et al., "Clinical evaluation of a transcutaneous interrogated fluorescence lifetime-based microsensor for continuous glucose reading," J Diabetes and Technology, 3(1):98-109 (2009).
Nielson, R. et al., "Microreplication and design of biological architectures using dynamicmask multiphoton lithography," Small, 5(1):120-125 (2009).
Onuki, Y. et al., "A review of the biocompatibility of implantable devices: Current challenges to overcome foreign body response," Journal of Diabetes Science and Technology, 2(6):1003-1015 (2008).

Ostendorf, A. et al., "Two-photon polymerization: a new approach to micromachining," Photonics Spectra, 40(10):72-79 (2006).
Ozdemir et al., "Axial pattern composite prefabrication of high-density porbus polyethylene: experimental and clinical research," Plast. Reconstr. Surg., 115(1):183-196 (2005).
Phelps et al., "Bioartificial matrices for therapeutic vascularization," PNAS USA, 107(8):3323-3328 (2010).
Pickup, J. C. et al., "In vivo glucose monitoring: the clinical reality and the promise," Biosens Bloelectron., 20(10):1897-1902 (2005), Available online Oct. 3, 2004.
Rounds et al., "Microporated peg spheres for fluorescent analyte detection," Journal of Fluorescence, 17(1):57-63 (2007), Available online Nov. 17, 2006.
Russell et al., "A fluorescence-based glucose biosensor using concanavalin A and dextran encapsulated in apoly(ethylene glycol) hydrogel," Anal. Chem., 71(15):3126-3132 (1999).
Sanders et al., "Tissue response to single-polymer fibers of varying diameters: evaluation of fibrous encapsulation and macrophage density," J Biomed. Mater. Research, 52:231-237 (2000).
Sanders et al., "Tissue response to microfibers of different polymers: polyester, polyethylene, polylactic acid, and polyurethane," J Biomed. Mater. Research, 62(2):222-227 (2002).
Sanders et al., "Fibrous encapsulation of single polymer microfibers depends on their vertical dimension in subcutaneous tissue," J Biomed. Mater. Research, 67A:1181-1187 (2003).
Sanders et al., "Relative influence of polymer fiber diameter and surface charge on fibrous capsule thickness and vessel density for single-fiber implants," J Biomed. Mater. Research, 65A:462-467 (2003).
Sanders et al., "Polymer microfiber mechanical properties: a system for assessment and investigation of the link with fibrous capsule formation," J Biomed. Mater. Research, 67A:1412-1416 (2003).
Sanders et al., "Small fiber diameter fibro-porous meshes: tissue response sensitivity to fiber spacing," J Biomed Mater Research, 72A:335-342 (2005).
Sanders et al., "Fibro-porous meshes made from polyurethane micro-fibers: effects of surface charge on tissue response," Biomaterials, 26(7):813-818 (2005).
Schultz et al., "Affinity sensor: a new technique for developing implantable sensors for glucose and other metabolites," Diabetes Care, 5(3)245-253 (1982).
Smith, J.L., "The Pursuit of Noninvasive Glucose: 'Hunting the Deceitful Turkey,'" (2006).
Srivastava et al., "Application of self-assembled ultrathin film coatings to stabilize macromolecule encapsulation in alginate microspheres," J of Microencapsulation, 22(4):397-411 (2005).
Srivastava et al., "Stabilization of glucose oxidase in alginate microspheres with photo reactive diazoresin nanofilm coatings," Biotechnology and Bioengineering, 91(1):124-131 (2005).
Takano et al., "An oxo-bacteriochlorin derivative for long-wavelength fluorescence ratiometric alcohol sensing," Analyst, 135:2334-2339 (2010).
Tian et al., "Dually fluorescent sensing of PH and dissolved oxygen using a membrane made from polymerizable sensing monomers," Sensors and Actuators B, 147:714-722 (2010).
Tian et al., "Influence of matrices on oxygen sensing of three-sensing films with chemically conjugated platinum porphyrin probes and preliminary application for monitoring of oxygen consumption of *Escherichia coli* (*E. coli*)." Sensors and Actuators B 150:579-587 (2010).
Tian, Y. et al., "A New Cross-linkable Oxygen Sensor Covalently Bonded into Poly(2-hydroxyethyl methacrylate)-co-Polyacrylamide Thin Film for Dissolved Oxygen Sensing," Chem. Mater, 22:2069-2078 (2010).
Vidavalur, R. et al., "Sildenafil induces angiogenic response in human coronary arteriolar endothelial cells through the expression of thioredoxin, hemaoxygenase, and VEGF," Vasc Pharm, 45(2):91-95 (2006).
Ward, W. K., et.al., "The effect of microgeometry, implant thickness and polyurethane chemistry on the foreign body response to subcutaneous implants," Biomaterials, 23(2):4185-4192 (2002).

(56) References Cited

OTHER PUBLICATIONS

Wisniewski, N. et.al., "Characterization of implantable biosensor membrane fouling," Fresen J Anal Chem., 366 (6-7):611-621 (2000).
Wisniewski, N. et. al., "Methods for reducing biosensor membrane biofouling," Colloids and Surfaces B: Biointerfaces, 18:197-219 (2000).
Woderer, S., "Continuous glucose monitoring in interstitial fluid using glucose oxidase-based sensor compared to established blood glucose measurement in rats," Anal Chim Acta., 581(1):7-12 (2007), Available online Aug. 18, 2006.
Office Action for Canadian Application No. 2,813,041, dated Jun. 6, 2017, 3 pages.
European Search Report for European Application No. 11831627.2, dated Feb. 23, 2017, 9 pages.
Patent Examination Report No. 1 for Australian Application No. 2015200893, dated Aug. 22, 2016, 5 pages.
Patent Examination Report No. 2 for Australian Application No. 2015200893, dated Mar. 1, 2017, 4 pages.
Notice on the First Office Action for Chinese Application No. 201510471187.8, dated Aug. 21, 2017, 25 pages.
Notice of Reasons for Rejection for Japanese Application No. 2015-205520, dated Oct. 4, 2016, 8 pages.
Notice of Reasons for Rejection for Japanese Application No. 2015-205520, dated Sep. 5, 2017, 11 pages.
Office Action for U.S. Appl. No. 15/087,514, dated Nov. 3, 2016, 16 pages.
Office Action for U.S. Appl. No. 15/087,514, dated Nov. 17, 2017, 11 page.
Alexeev et al., "High ionic strength glucose-sensing photonic crystal," Anal. Chem., 75:2316-2323 (2003).
Leavesley, S. J. et al., "Hyperspectral imaging microscopy for identification and quantitative analysis of fluorescently-labeled cells in highly autofluorescent tissue," J. Biophontonics, Jan. 2012;5(1):67-84. doi: 10.1002/jbio.201100066. Epub Oct. 11, 2011.
Shibata, H. et al., "Injectable hydrogel microbeads for fluorescence-based in vivo continuous glucose monitoring", Proceedings of the National Academy of Sciences of the United States of America, Oct. 19, 2010, vol. 107, No. 42, pp. 17894-17898.
Young et al., "A novel porous collagen scaffold around an implantable biosensor for improving biocompatibility. I. In vitro/in vivo stability of the scaffold and in vitro sensitivity of the glucose sensor with scaffold," Journal of Biomedical Materials Research Part A., 2008, vol. 87, pp. 136-146.

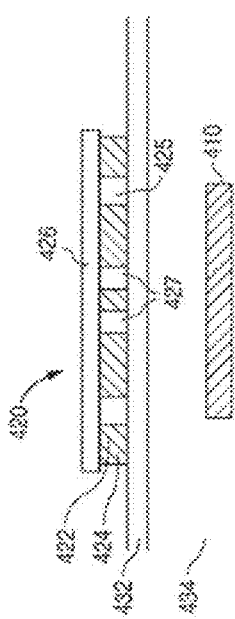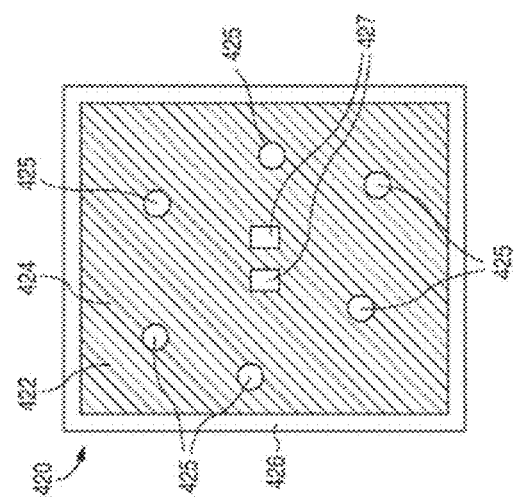

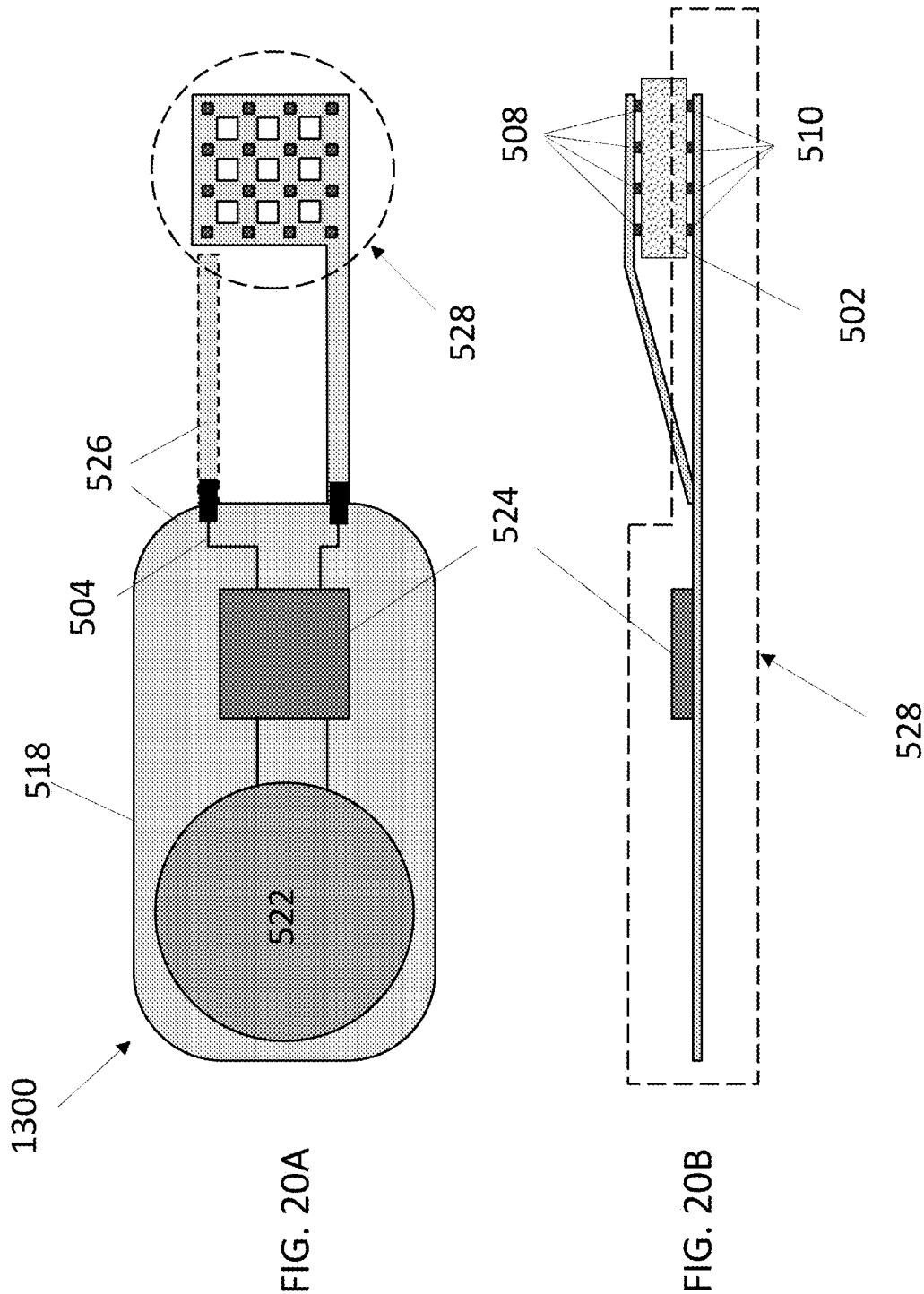

TISSUE-INTEGRATING ELECTRONIC APPARATUS

CROSS-REFERENCE TO RELATED APPLICATIONS

This application is a continuation-in-part of U.S. patent application Ser. No. 12/789,048, entitled "Method and System for Directing a Localized Biological Response to an Implant," filed May 27, 2010, the disclosure of which is hereby incorporated by reference in its entirety. This application is a continuation of U.S. patent application Ser. No. 13/267,741, entitled "Tissue-Integrating Sensors," filed Oct. 6, 2011, which claims priority to U.S. Provisional Application No. 61/390,252, filed on Oct. 6, 2010, the disclosures of each of which is hereby incorporated by reference in its entirety.

TECHNICAL FIELD

This invention relates generally to implants. More specifically, the invention relates to methods for directing a localized biological response of a mammalian body to an implant disposed within the body and to an implant system for long-term use. This invention also relates to implantable tissue-integrating electronic apparatuses capable of detecting one or more signals (e.g., analyte, electrical, optical, mechanical, magnetic and/or thermal signals) in an in vivo sample.

BACKGROUND

Methods have long been sought for extending the useful life of an implant that is inserted into the body. Not only is it important for an implant to last long enough to justify the cost, potential complications, and pain of implantation, but many situations exist in which there are strong medical reasons for maintaining the same implant within the body for an extended period of time. For example, when the implant is a sensor, having reliable, consistent, and continuous data from the same sensor can improve patient care.

Studies have shown that continuous measurement of biochemical analytes or drugs in the body significantly improves management and treatment of acute or chronic illnesses. For example, continuous monitoring may provide better control of diabetes, reducing the incidence of sequelae that lead to vision loss and impaired circulation. In trauma and congestive heart failure patients, the levels of lactate and glucose should be monitored simultaneously and continuously to facilitate detection of occult bleeding and changes in shock status. Real-time monitoring over the course of systemic administration of drugs or chemotherapeutic agents that have narrow ranges of effective concentration can provide the clinician with feedback upon which to make adjustments to dosing to assure proper concentrations are achieved and maintained.

Over a period of more than 20 years, many attempts have been made to develop an implanted sensor that provides frequent or continuous monitoring. For example, U.S. Pat. No. 4,703,756 to Gough et al., filed May 6, 1986, describes a sensor module for implantation in the body to monitor glucose and oxygen levels. When an apparatus having a sensor (or any other foreign body) is implanted, inflammatory and immune responses are initiated. Within minutes, protein (primarily fibrinogen) and platelets begin to adhere to the implant, followed over hours to days by recruitment of inflammatory and immune cells, which then surround the sensor. These initial tissue responses result in protein fouling of the sensor interface and potential degradation of the sensor chemistry by enzymes. Over the subsequent days and weeks, granulation tissue forms as the body attempts to repair the tissue damaged by the implantation procedure. Eventually, continued collagen production over the following weeks to months leads to formation of an avascular capsule surrounding the sensor and causes loss of analyte availability to the sensor. The avascular capsule is believed to be ultimately responsible for the majority of the drift of signal, loss of sensor sensitivity, and the need for frequent recalibration or even sensor replacement.

Various technologies have attempted to overcome this problem. For example, sensors have been developed that are placed intravascularly to avoid the problems of a capsule by allowing the tip of the sensor to be in continuous contact with the blood. However, placing a sensor directly into the vasculature puts the recipient at risk for thrombophlebosis, thromboembolism, and thrombophlebitis.

Sensors have also been developed that have physical features designed to address the problem of the foreign body response. For example, U.S. Pat. No. 6,212,416 to Ward et al. and U.S. Pat. No. 7,134,999 to Brauker et al. both offer architectural solutions. Ward et al. describe a movable outer membrane that can be renewed when it becomes fouled. Brauker et al. describe a sensor having a geometric design intended to minimize chronic inflammatory response at the sensing region of the sensor. However, these solutions do not permit the device to remain fully functional for long-term use, i.e., over a period of months or even years.

Attempts have been made to control the foreign body response by implanting therapeutic agents, e.g., tissue response modifiers, at the same time as the sensor. Such tissue response modifiers attempt to mask the presence of the implant within the body and reduce or eliminate the foreign body response. Vachon, in U.S. Pat. No. 6,212,416 describes a biosensor comprising an accessory material that includes a coating containing a hydrophilic material and/or a fiber modified to deliver a therapeutic agent. In U.S. Pat. No. 6,497,729, Moussey et al. describe a tissue/implant interface comprising a polymer layer that contains at least one tissue response modifier covalently attached to the polymer layer or entrapped within the polymer layer.

Such devices are successful in directing the foreign body response for a period of time that is limited by the amount of therapeutic agent that can be delivered along with the sensor. The mass of a drug or other compound necessary to consistently control the foreign body response over a period of 2-5 years is on the scale of hundreds to thousands of milligrams. This quantity is too large for a one-time administration or for incorporation into a drug reservoir feature of the sensor. Because the foreign body response increases when the size of the implant increases, delivering a sensor made larger by its accompanying therapeutic agent would be counterproductive. Furthermore, even if means were conceived to achieve a one-time delivery of a large quantity of a therapeutic agent, no known drugs or compounds for controlling a foreign body response are capable of remaining stable at body temperatures of 35° C. to 37° C. over a period of 2-5 years.

Therefore, it would be desirable to have an improved method for directing a localized biological response of a mammalian body to an implant and an implant system for long-term use that overcomes the aforementioned and other disadvantages. It would also be desirable to have a self-contained implant with electrical components that may be used to generate and/or measure one or more signals (e.g., analyte, electrical, optical, mechanical, magnetic and/or thermal signals).

Because the foreign body response increases when the size of the implant increases, having large electrical components in an implant can be counterproductive. A self-contained implant with, for example, a power source may be desirable to lessen the risk of infection from a percutaneous wire. Attempts to miniaturize apparatuses with sensors (e.g. analyte, electrical, optical, mechanical, magnetic and/or thermal sensors) may result in apparatuses for which a signal is not strong enough to be detected.

Implanted apparatuses that are larger than the cellular phagocytic size threshold become surrounded by immune cells and/or encapsulated and they lose their ability to accurately and rapidly sense blood-borne analytes in an unpredictable fashion. For implanted apparatuses that are below the phagocytic size threshold, they become engulfed by phagocytic cells and measure intracellular analyte levels instead of measuring analyte levels in the interstitial fluid as intended. Intracellular analyte levels are often irrelevant for systemic analyte monitoring, as is the case for continuous glucose monitors. The loss of contact between sensors and the interstitial fluid containing the analyte of interest, or the transport barriers imposed by the foreign body response are the primary reasons current sensing technologies typically fail after only a short time in the body (e.g., 2-7 days for commercially available sensors).

Thus, there remains a clear need for sensing technologies (e.g. analyte, electrical, optical, mechanical, magnetic and/or thermal sensing technologies) that are tissue integrating to provide long-term (e.g., weeks, months or years) and accurate readings by remaining in contact with interstitial fluid (not the internal cellular environment) and remaining in close proximity to the vasculature so that the interstitial fluid surrounding the sensor is in constant rapid equilibrium with nearby capillaries.

SUMMARY

Disclosed herein are tissue-integrating electronic apparatuses, systems comprising these apparatuses and methods of using these apparatuses and systems to generate and measure various signals.

In an embodiment, a tissue-integrating apparatus includes a tissue-integrating scaffold including a flexible wire and a sensor operatively coupled to the flexible wire and integrated with the scaffold, the sensor configured to produce a detectable signal. The tissue-integrating apparatus as described herein may provide long-term detection of analyte(s). The tissue-integrating apparatus may include at least one of a light source, a detector, a temperature sensor, an accelerometer, a pressure sensor, a magnetic sensor, or a piezoelectronic sensor. The tissue-integrating scaffold may include one or more polymeric materials, for example one or more hydrogels. The apparatus may further include sensing moieties embedded and/or attached to the exterior of the scaffold or that form a polymeric material coated on the scaffold. In certain embodiments, the scaffold is porous and at least two of the pores are interconnected. In certain embodiments, the sensor includes a plurality of perforations. Any of the apparatuses described herein may include one or more layers (with or without sensing moieties in one or more of the layers) and/or one or more fibers.

In some embodiments, a tissue-integrating apparatus includes a tissue-integrating scaffold including a flexible wire or wires and a tissue-integrating electrode or electrodes coupled to the flexible wire, the flexible wire being configured to conduct at least one electrical signal (e.g., an amperometric or a potentiometric signal) flowing through the tissue-integrating electrode, with at least one electrical signal being associated with an amount of an analyte. In some embodiments, the tissue-integrating electrode is at least one of a tissue-integrating working electrode, a tissue-integrating counter electrode or a tissue-integrating reference electrode. In some embodiments, the tissue-integrating electrode is one of a plurality of tissue-integrating electrodes connected in series. In certain embodiments, the tissue-integrating electrode is one of a plurality of tissue-integrating electrodes connected in parallel. The apparatus may further include at least one of a temperature sensor, an accelerometer, a pressure sensor, a magnetic sensor and/or a piezoelectronic sensor.

In some embodiments, a system for detecting an analyte includes one or more tissue-integrating apparatuses as described herein; and an implantable module that measures the signal produced by the tissue-integrating apparatus. In some embodiments, the system further includes one or more of the following: a power source, electrical control circuitry, a detector, a signal receiver, a signal transmitter, a signal processor, a data storage component, a data transmitter, a data processor and/or a display and/or combinations thereof. In some embodiments, the system further includes an external device having one or more of the following: a power source, a signal receiver, a signal processor, a data processor, memory for storing data and/or a display.

In other embodiments, methods of making and using the apparatuses and systems as described herein are disclosed. A method for detecting an analyte includes integrating one or more apparatuses as described herein into the tissue of a subject and detecting the presence of the analyte.

BRIEF DESCRIPTION OF THE DRAWINGS

FIG. 4 is an illustration of an embodiment of an implant system for long-term use, in accordance with the invention, the implant shown as a sensor, and the nonsurgical means for delivering a tissue response modifier shown as a patch.

FIG. 5 is a top view of the patch of FIG. 4.

FIG. 10A illustrates a tissue-integrating opto-electronic apparatus in which one or more light sources are integrated with the scaffold.

FIGS. 10B and 10C illustrate tissue-integrating opto-electronic apparatuses in which one or more light sources are proximate the scaffold. FIG. 10D illustrates a tissue-integrating opto-electronic apparatus in which one or more light sources are sandwiched between layers of the scaffold.

FIGS. 20A-20B are top and side schematic view of an example of an opto-electronic system having a tissue integrating scaffold sandwiched between one or more light sources and one or more detectors, according to an embodiment. The system also includes an implantable tissue anchoring module operatively coupled to the one or more light sources and the one or more detectors.

Figure 1:
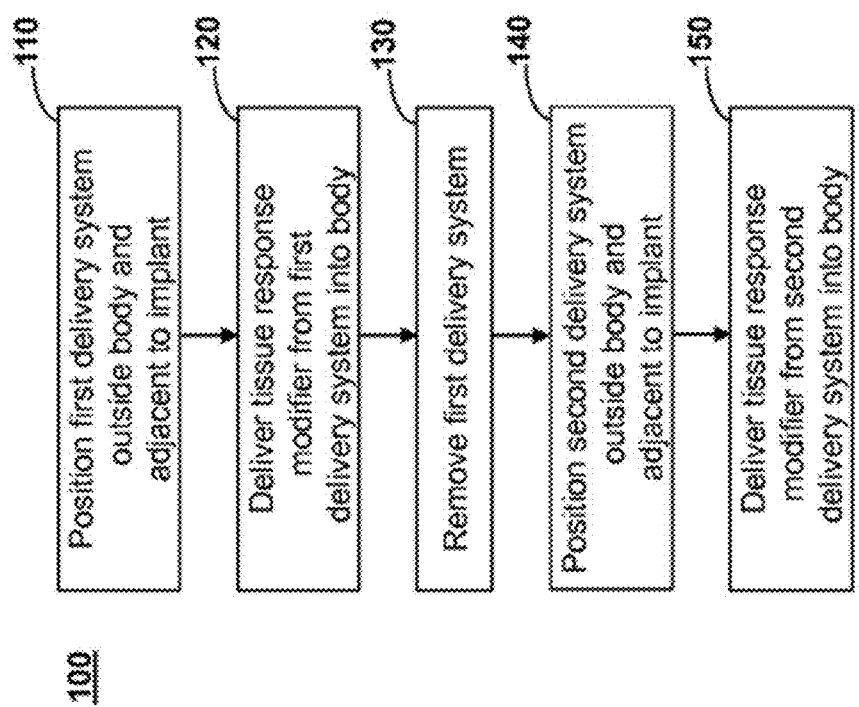
FIG. 1 is a flow diagram of one embodiment of a method for directing a localized biological response of a mammalian body to an implant disposed within the body, in accordance with the invention, in which the method is used to prolong the useful life of the implant.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Described herein are tissue-integrating electronic apparatuses and systems useful for accurate and optionally long term measurements of analytes in vivo. The implantable apparatuses, systems and methods described herein provide for continuous or semi-continuous collection of data of various signals (e.g., analyte, electrical, optical, mechanical, magnetic and/or thermal signals) with the use of tissue-integrating electrical components.

In particular, the tissue-integrating electronic apparatuses that are the subject of this invention remain in good contact (e.g., close proximity) to blood vessels and/or collagen. The apparatuses also have direct access to measurements of interstitial fluid. The apparatuses include tissue-integrating components (e.g., a tissue-integrating scaffold) and tissue anchoring components (e.g., electrical, optical, mechanical, magnetic and/or thermal components). The tissue-integrating and tissue anchoring components encourage cellular integration and increase the contact surface area between the tissue and apparatus. The tissue-integrating scaffold may encourage capillary growth into and/or nearby the sensing media. The tissue anchoring components of the apparatuses may encourage capillary and/or collagen ingrowth. Additionally the tissue-integrating electronic apparatus may have a modulus closer to the texture of tissue, thus enhancing the integration in the tissue. Furthermore, the tissue anchoring components may reduce the interfacial stresses between the tissue and apparatus and as a result, decrease the impact of the foreign body response to the apparatus, improving its performance.

Thus, unlike other devices, the apparatuses described herein allow cells and/or capillaries to grow in close proximity to regions of the apparatus (e.g., on the surface and inside), which results in accurate analyte measurements, including over the long term. Tissue-integrating electronic apparatuses minimize the foreign body response and/or promote vascularization. Capillary growth directly into and throughout regions of the apparatus allows unencumbered access to analytes of interest in the blood (e.g., glucose, lactate, pyruvate, cortisol, ions, proteins, nucleic acids, alcohols, urea, etc.). The level of tissue integration and proximity of capillaries to regions of the apparatus provide a close, stable relationship between the analyte concentration in the blood and in the tissue surrounding and integrated with the apparatus.

Advantages of the device and methods described herein include, but are not limited to: (1) providing devices that integrate into the subject (e.g., through tissue and/or capillary in-growth; (2) providing devices having at least one component that anchors or holds the systems in place to or within the tissue of the subject; (3) providing devices that can be implanted through syringe injection, meaning that no surgery is required to put the sensing media in place in the body; (4) providing devices having material(s) having properties more similar to actual tissue (e.g., modulus that is more similar to tissue's modulus and water content) to allow a better integration into the tissue; (5) providing devices that accurately assess analyte(s) for long periods of time (e.g., greater than a week, typically weeks, months or years) and/or (6) providing devices of small dimensions that will result in increased patient comfort and better acceptance by the body.

As used in this specification and the appended claims, the singular forms "a", "an", and "the" include plural referents unless the content clearly dictates otherwise. Thus, for example, reference to a sensor comprising "a sensing moiety" includes devices comprising two or more sensing moieties. Likewise, reference to "an analyte" includes two or more analytes.

Definitions

As used in the specification and claims of this application, the following definitions should be applied:

The term "tissue-integrating" refers to material (e.g., scaffold) that promotes cellular ingrowth (e.g., vascularization) that, when integrated into living tissue, remains in close proximity with the blood vessels of the tissue (e.g., capillaries). By "close proximity," is meant that the average distance from any point within the material (scaffold) implanted into the tissue to the nearest blood vessel is no greater than 100 microns more than the average distance from any point in the native (original) tissue to the nearest blood vessel.

The term "tissue anchoring" refers to material or feature (e.g., sensor, perforated substrate, textured surface) that, when integrated into living tissue, holds one or more objects in place and restricts movement of the one or more objects relative to the native tissue as a result of the high contact surface area and ability of cells to infiltrate and interact with the apparatus. Tissue anchoring may also refer to material or features that reduce the interfacial stresses between apparatus and tissue, minimizing the impact of the foreign body response on the performance of the apparatus. Tissue anchoring also refers to material or features that, when integrated into living tissue, remains in close proximity with vasculature of the tissue. The average distance from any point in the tissue anchoring material to vasculature ranges from about 1 micron to about 1000 microns.

The term "conductive" refers to material that conducts or transmits electricity or electrical signals.

The term "flexible" refers to material that is capable of bending, stretching, compressing or twisting without breaking.

Methods for Directing a Localized Biological Response to an Implant

One aspect of the invention is a method for directing a localized biological response of a mammalian body to an implant disposed within the body. FIG. 1 shows a flow diagram of one embodiment of the method in accordance with the invention.

In some embodiments, the implant is disposed within the mammalian body adjacent to an outside surface of the body. For example, the implant may be disposed in one or more of the hypodermis, the subcutis, the subcutaneous adipose fat, the dermis, an intradermal location, a subdermal location and a muscle location. In some embodiments, the implant is positioned such that it is fully enclosed within the mammalian body.

The implant may be any device or material disposed in or under the skin. For example, the implant may be a sensor (e.g., analyte, electrical, mechanical, and/or thermal sensor), a drug delivery device, a pump, a chip, combinations thereof, and the like. The implant may also be a tissue integrating apparatus having a sensor (e.g., optical, electrical, mechanical, magnetic, and/or thermal sensor) as will be described, for example, with reference to FIGS. 6A-20B. Typically the mammalian body is allowed to stabilize for an appropriate period of time following insertion of the implant before carrying out the method. The time may be minimal where the implant is delivered via a syringe or catheter, or as long as several days where the implant is delivered surgically.

In some embodiments, a tissue response modifier (comprising one or more individual modifiers) is delivered into the body in a quantity effective to direct a localized biological response of the body to the implant, thereby prolonging the useful life of the implant. As used herein, the terms "direct" and "directing" denote both reducing and increasing various aspects of the localized biological response as well as eliminating various aspects altogether.

In the method shown at 100, a first delivery system is positioned outside the mammalian body adjacent to the implant (Block 110). The first delivery system may comprise one or more of a cream, a gel, an ointment, a sprayer, a patch, a bandage insert, an array of microneedles, a syringe, and the like. The delivery system may also comprise one or more of a radiation source (e.g., a source of light, ultrasound, electricity, magnetism, heat, and/or cooling) and a pressure source (used, for example, for laser-induced pressure delivery).

Where the delivery system is a patch or a bandage insert, positioning the delivery system outside the body and adjacent to the implant involves applying the patch or bandage insert to an outside surface of the body adjacent to the implant (e.g., to the epidermis in the area of the body within which the implant resides). Positioning a cream, a gel, an ointment, or another similar preparation that delivers a tissue response modifier transdermally (i.e., through unbroken skin) involves applying the preparation to an outside surface of the body. Where the delivery system is, for example, a sprayer or a syringe, positioning the delivery system outside the body adjacent to the implant involves placing the system in position to spray material onto the skin or inject material into or through the skin. A radiation source or pressure source would be placed in position to allow delivery of the radiation or pressure to skin tissue adjacent to the implant.

The delivery system comprises a tissue response modifier effective for directing a localized biological response of the body to the implant. As defined herein, the term "tissue response modifier" denotes a substance or physical phenomenon that increases, decreases, or eliminates one or more aspects of the tissue response. In some embodiments, the tissue response modifier is selected to prevent or minimize a biological response that would impede availability of analyte to the implant or otherwise limit the useful life of the implant, or to increase a biological response that would prolong the useful life of the implant.

The tissue response modifier may comprise, for example, one or more of a collagen inhibitor, an anti-fibrotic agent, an angiogenic agent, a vasculogenic agent, a pro-vascular dilation agent, an immunosuppressive agent, an anti-proliferative agent, an anti-migratory agent, an anti-inflammatory agent, a vasodilator, an anti-histamine, an anti-protein-fouling agent, a synthetic molecule, a biologically produced molecule, a permeation enhancer, a gene therapy agent, a stem cell, a mammalian cell, a drug, and the like. The tissue response modifier may also comprise visible light, other wavelengths of light, ultrasound, heat, an electrical pulse, a magnetic field, a magnetic pulse, and combinations thereof.

Specific examples of tissue response modifiers include aspirin, imatinib, celecoxib, rofecoxib, etoricoxib, transforming growth factor β3, interleukin 10, mannose-6-phosphate, cortisone, prednisone, dexamethasone, ibuprofen, cromolyn sodium, halofuginone hydrobromide, tranilast, perfenidone, D-penicillamine, 1-butyryl-glycerol, adenosine, methrotrexate, mycophenolate mofetil, tacrolimus, paclitaxel, rapamycin, doxorubicin, azathioprene, losartan potassium, mitomycin C, diclofenac, dexamethasone, ketoprofane, prostscylin, nifedipine, loratadine, nedocromil, detergents, tissue necrosis factors and/or their inhibitors, platelet derived growth factor, portions of these molecules, sense or anti-sense molecules, and combinations thereof. The above lists are not intended to be exhaustive; additional, unnamed tissue response modifiers are anticipated to be effective in the claimed methods.

The tissue response modifier is delivered from the delivery system into the body in a quantity effective to direct the localized biological response of the body to the implant (Block 120). The tissue response modifier may be delivered transdermally (through unbroken skin) and/or may be injected into the body through skin tissue adjacent to the implant.

For example, the delivery system may be a patch that includes a tissue response modifier that diffuses into the body through the epidermis and onto and/or around the implant. Alternatively or additionally, the patch may include an array of microneedles, with the tissue response modifier injected by the microneedles into skin tissue adjacent to the implant. The tissue response modifier may also be delivered transdermally via a cream, gel, ointment or sprayer or may be injected into the area of the implant using a hypodermic needle, a catheter, or another injection device, taking care to avoid the implant.

The tissue response modifier is not delivered from the delivery system surgically, i.e., it is not delivered via an incision, nor is the material contained in the delivery system delivered along with the implant at the same time the implant is inserted into the body. In the present method, the tissue response modifier is delivered separately from and later than the implant.

The tissue response modifier is delivered at a low level (e.g., at a low dosage) because the tissue response modifier is not intended to reach systemic levels but is intended to reach adequate local levels to direct the biological response of the localized tissue of the body to the implant. The tissue response modifier is supplied in a quantity effective to direct the tissue architecture, vascularity, collagen content, protein deposition, cellular activity, and/or other tissue characteristics at the tissue-implant interface and up to several centimeters away from the implant. This quantity is low compared to the typically delivered system doses. For example, aspirin, an anti-inflammatory and anti-platelet molecule working by means of cycloxygenase inhibition, is typically delivered systemically at a therapeutic level of 325 mg aspirin/80 kg body weight. Local delivery doses of aspirin to the region of a typically sized electrochemical sensor implant would be approximately 1,000 to 10,000 times less in dosage than systemically delivered doses administered to achieve the same local concentrations.

Delivery of the tissue response modifier may be aided by processes such as electroporation, iontophoresis, sonophoresis, laser-induced pressure, delivery of permeation enhancers, and the like. The delivery system may include, in addition to the tissue response modifier, a material effective to target delivery of the tissue response modifier to a specific location within the body and/or to modulate uptake of the tissue response modifier by the body. For example, cell-specific adhesion molecules or other specific adhesion molecules (e.g., to target adhesion to collagen or proteoglycans in the interstitial space) may be included along with the tissue response modifier to achieve targeted delivery of the tissue response modifier to a specific location such as the dermis or subcutis. The material may modulate uptake into the bloodstream, into specific cell types, into specific structures (e.g., collagen bundles) and/or into or through the epidermis, dermis, and or subcutaneous.

In addition to materials or functions related to delivery of the tissue response modifier, the delivery system may also include components related to activities of the implant. For example, where the implant is a device (e.g., a sensor or a pump), the delivery system may include one or more components such as an actuator, illuminator, a detector, a signal receiver, a signal transmitter, an energy storage component, a data storage component, and the like.

In some embodiments, in which the localized biological response of the body to the implant is being directed to prolong the useful life of the implant, typically a second (third, fourth, etc.) delivery system is utilized. Before the tissue response modifier provided by the first delivery system loses its effectiveness, the second delivery system is positioned outside the body and adjacent to the implant (Block 140), and the second tissue response modifier is delivered from the second delivery system into the body (Block 150). The second delivery system may include the same or a different tissue response modifier (comprising one or more individual modifiers) effective for directing the localized biological response of the body to the implant. The second tissue response modifier, like the first, is delivered nonsurgically.

The first delivery system may be removed (Block 130) prior to positioning the second delivery system. For example, where the delivery system comprises a patch, the first patch would be removed prior to positioning a second patch. Where the first delivery system is a topical preparation such as a cream, the cream need not be washed off before a second tissue response modifier is delivered. Typically a second delivery system will comprise the same tissue response modifier as the first system, but an advantage of delivering the tissue response modifier from outside the body is that the tissue response modifier and/or its mode of delivery can be changed or combined with another tissue response modifier and/or mode of delivery to optimally direct the body's response to the implant.

Figure 2:
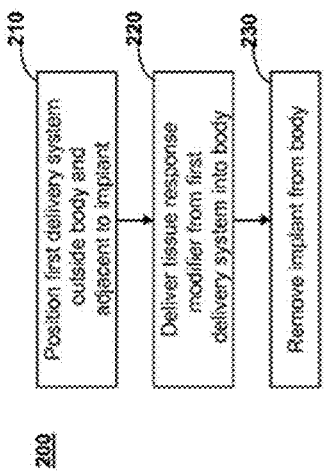
FIG. 2 is a flow diagram of an embodiment of a method for directing a localized biological response of a mammalian body to an implant disposed within the body, in accordance with the invention, in which the method is used to facilitate removal of the implant.

FIG. 2 shows a flow diagram of an embodiment of a method for directing a localized biological response of a mammalian body to an implant disposed within the body, in accordance with the invention. In some embodiments, a tissue response modifier is delivered into the body in a quantity effective to direct a localized biological response of the body to the implant to aid in preparing the body and/or the implant for removal of the implant.

In the method shown at 200, a first delivery system, comprising a first tissue response modifier effective for directing a localized biological response of the body to the implant, is positioned outside the mammalian body adjacent to the implant (Block 210). The first delivery system may be as described above for method 100, with the tissue response modifier selected for facilitating removal of the implant.

The tissue response modifier is delivered from the first delivery system into the body in a quantity effective to direct the localized biological response of the body to the implant (Block 220). Delivery of the tissue response modifier may be carried out as described above for method 100. Some embodiments will find particular utility where the localized biological response of the body to the implant has not been directed during the tenure of the implant within the body as described above and illustrated at 100. For example, the tissue response modifier in some embodiments may be a drug or other treatment intended to reduce vascularization in the area of the implant to reduce bleeding during its removal. It may also be a drug or other treatment effective to reduce collagen buildup surrounding the implant to limit the amount of tissue that will be removed along with the implant.

At some time after the tissue response modifier has been delivered from the first delivery system into the body, the implant is removed from the body (Block 230), typically by surgical means (i.e., an incision is made in the body, and the implant is removed through the incision). It is anticipated that a second (third, fourth, etc.) delivery system may be used as needed prior to removal of the implant.

Figure 3:
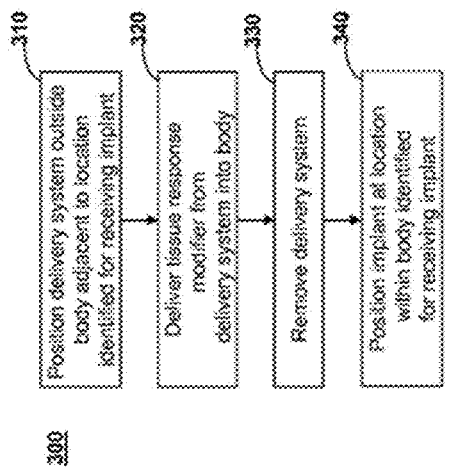
FIG. 3 is a flow diagram of a method for directing a localized biological response of a mammalian body, in accordance with the invention, in which the method is used to aid in preparing the body for an implant.
Figure 6B:
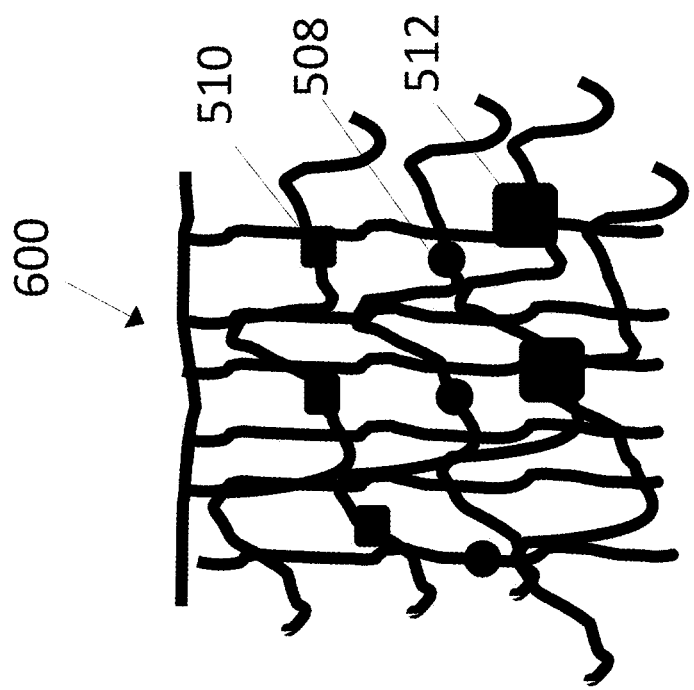
FIG. 6B illustrates a perspective view of an example of a tissue-integrating electronic apparatus including a scaffold having flexible wires in a fabric or mesh, according to an embodiment.
Figure 6A:
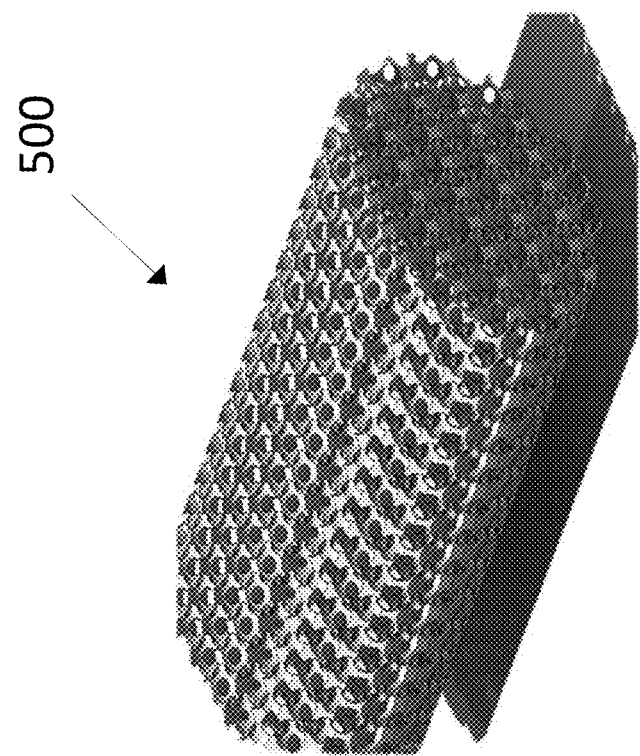
FIG. 6A illustrates a perspective view of an example of a tissue-integrating electronic apparatus including a scaffold having flexible wires coated with a polymeric material, according to an embodiment.
Figures 7A, 7B:
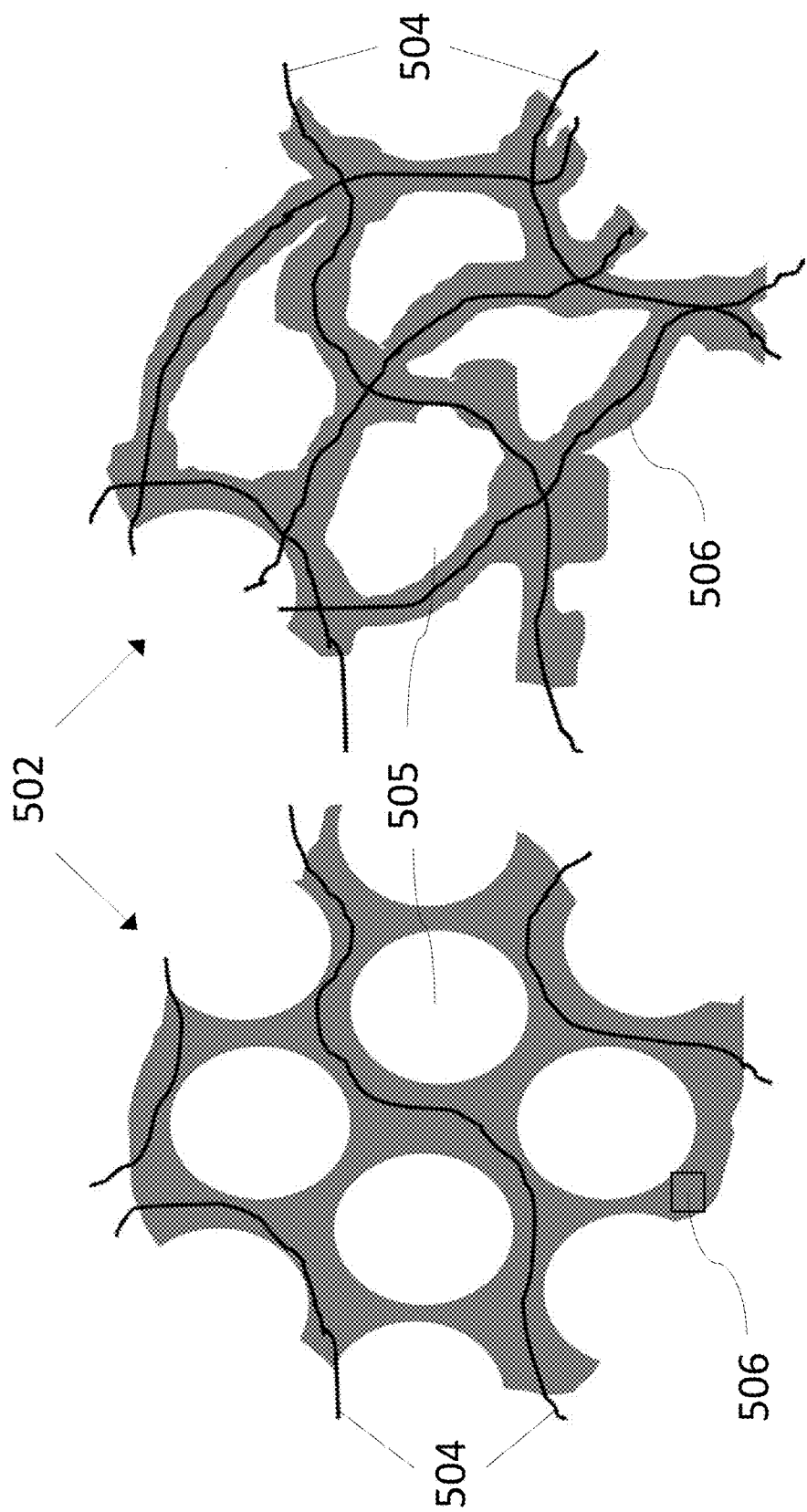
FIG. 7A is a simplified cross-sectional view of the scaffold of the tissue-integrating electronic apparatus shown in FIG. 6A in which the scaffold includes flexible wires coated with a polymeric material, according to an embodiment.
FIG. 7B is a simplified cross-sectional view of the scaffold of the tissue-integrating electronic apparatus shown in FIG. 6B in which the scaffold includes flexible wires in a fabric mesh coated with a polymeric material, according to an embodiment.

FIG. 3 shows a flow diagram of one embodiment of a method for directing a localized biological response of a mammalian body to an implant, in accordance with the invention, in which the method is used to aid in preparing the mammalian body for insertion of an implant.

In the method shown at 300, a first delivery system, comprising a first tissue response modifier effective for directing a localized biological response of the body to the implant, is positioned outside the mammalian body adjacent to a location within the body identified for receiving the implant (Block 310). The first delivery system may be as described above for method 100.

The tissue response modifier is delivered from the delivery system into the body in a quantity effective to direct the localized biological response of the body to the implant (Block 320). Delivery of the tissue response modifier is nonsurgical and may be carried out as described above for method 100.

The delivery system is removed (Block 330) as needed, and the implant is positioned at the location within the body identified for receiving the implant (Block 340). By delivering a tissue response modifier into the body in advance of the implant, a localized biological response of the body to the implant may be directed to minimize or avoid an undesirable response of the body to the implant or to initiate or enhance a desired response.

A material that attracts and/or contains the tissue response modifier may be implanted within the body adjacent to the implant, and the tissue response modifier may then be delivered into the implanted material. In the case of a tissue response modifier delivered transdermally or using microneedles, the tissue response modifier would diffuse into and pool within the implanted material. In the case of a tissue response modifier injected using a hypodermic needle or a catheter, the tissue response modifier could be injected directly into the implanted material. The implanted material serves as a reservoir for the tissue response modifier, allowing it to be released into the area of the implant over time.

Implant Systems Having a Tissue Response Modifier

An embodiment of an implant system, in accordance with the invention, is illustrated in FIG. 4, which shows a cross-section view of an implant 410 disposed within the body and nonsurgical delivery means 420 disposed outside the body for delivering a tissue response modifier 422 through the epidermis 432 of the body. Tissue response modifier 422 is effective for directing a localized biological response of the body to the implant.

Implant 410 may be any device or material suitable for insertion within a mammalian body. It is desirable that implant 410 be small enough so that tissue displacement and acute inflammation resulting from its implantation is minimized. Implant 410 may be designed to be left in the body after its operational life is over and may include a feature or features designed to maintain location and directionality of the implant. Implant 410 is shown in FIG. 4 disposed in the dermis 434, but one of ordinary skill in the art will appreciate that alternative locations within the body are possible, (e.g., the implant may be disposed in one or more of the hypodermis, the subcutis, the subcutaneous adipose fat, the dermis, an intradermal location, and a subdermal location.)

Implant 410 may be, for example, a sensor (e.g., analyte, electrical, mechanical, and/or thermal sensor), a drug delivery device, a pump, a chip, and combinations thereof. Implant 410 may also be, for example, a tissue-integrating electronic apparatus having a sensor as will be described with reference to FIGS. 6A-20B.

Some embodiments, implant 410 is a glucose sensor comprising a glucose-binding substance. The sensing material is suspended in, contained within, attached to, or otherwise mixed with a hydrogel containing anti-inflammatory drugs or other tissue response modifying drugs. An appropriate amount of this mixture is implanted in the body by hypodermic needle or by microneedle patches that deliver the mixture into the dermis. During the healing process (e.g., over the next 3-7 days), the biosorbable hydrogel dissolves and is absorbed by the body, leaving the sensing material in place in the dermis or subcutis.

Nonsurgical delivery device 420 for delivering a tissue response modifier through the epidermis of the mammalian body may be, for example a cream, a gel, an ointment, a sprayer, a patch, a bandage insert, an array of microneedles, a syringe, combinations thereof, and the like. The nonsurgical delivery means may also comprise one or more of a radiation source (e.g., a source of light, electricity, magnetism, heat, cooling) and a pressure source (used, for example, for laser-induced pressure delivery).

Some embodiments, the nonsurgical delivery device is a patch 420, illustrated in side view in FIG. 4 and in top view in FIG. 5. Like reference numbers are used in the drawings to refer to like elements. Patch 420 includes tissue response modifier 422 disposed in a treatment portion 424 of the patch. Patch 420 also includes a backing portion 426 that provides support for treatment portion 424.

Tissue response modifier 422 may be a single modifier or a combination of modifiers. Tissue response modifier 422 may comprise, for example, a collagen inhibitor, an anti-fibrotic agent, an angiogenic agent, a vasculogenic agent, a pro-vascular dilation agent, an immunosuppressive agent, an anti-proliferative agent, an anti-migratory agent, an anti-inflammatory agent, a vasodilator, an anti-histamine, an anti-protein-fouling agent, a metabolic depressor, a synthetic molecule, a biologically produced molecule, a permeation enhancer, a gene therapy agent, a stem cell, a mammalian cell, a drug, and combinations thereof. The tissue response modifier may also comprise light, heat, an electrical pulse, a magnetic field, a magnetic pulse, and combinations thereof.

Specific examples of tissue response modifiers include aspirin, imatinib, celecoxib, rofecoxib, etoricoxib, trans-forming growth factor β3, interleukin 10, mannose-6-phosphate, cortisone, prednisone, dexamethasone, ibuprofen, cromolyn sodium, halofuginone hydrobromide, tranilast, perfenidone, D-penicillamine, 1-butyryl-glycerol, adenosine, methrotrexate, mycophenolate mofetil, tacrolimus, paclitaxel, rapamycin, doxorubicin, azathioprene, losartan potassium, mitomycin C, diclofenac, dexamethasone, ketoprofane, prostscylin, nifedipine, loratadine, nedocromil, detergents, tissue necrosis factors and/or their inhibitors, platelet derived growth factor, portions of these molecules, sense or anti-sense molecules, and combinations thereof. The above lists are not intended to be exhaustive; additional, unnamed tissue response modifiers are anticipated to be effective in the system.

The delivery device may also include a material effective to target delivery of the agent to a specific location within the body or to modulate uptake of the therapeutic agent by the body. The delivery device may further include a component that is related to or interacts with the implant. For example, the delivery device may include an actuator, an illuminator, a detector, a signal receiver, a signal transmitter, an energy storage component, a data storage component, and combinations thereof.

Some embodiments, patch 420 includes six illuminators 425 and two detectors 427, which together make up an interrogator that is capable of transmitting an interrogating signal to sensor 410 and receiving a sensor signal response. One skilled in the art will appreciate that the precise number of illuminators and detectors is not material to the practice of the invention.

Where interrogation of sensor 410 is optical, for example, illuminators 425 may include an LED (light emitting diode) or laser diode or other light source, and detectors 427 may include filtered p/n diodes that detect the transmitted or reflected light (absorbance spectroscopy) or emissions (fluorescence). The LED may be a filtered micro-LED in the NIR (near-infrared) region. Such LEDs efficiently illuminate through the skin. In the glucose sensor described above, the glucose-binding chemistry fluoresces at a different wavelength or absorbs a specific NIR region proportional to the amount of glucose bound to the sensing media. The fluorescent light or absorbed NIR light transmits back through the skin and is detected by the filtered p/n diodes arrayed in the patch.

In some embodiments, the interrogator may comprise a voltage source (as the illuminator) for providing a source signal; an antenna operable with the sensor for transmitting a source signal to the sensor and receiving a signal therefrom; first and second frequency filters (as the detector) operable with the voltage source for receiving the source signal therefrom and providing first and second reference signals; first and second multipliers receiving the interrogation signal and the first and second reference signals, respectively, for providing first and second product signals therefrom; and first and second integrators for receiving the first and second product signals and providing signals indicative of pressure at the sensor. The interrogator may further comprise third and fourth multipliers that receive a delayed interrogation signal and the first and second reference signals and provide third and fourth product signals therefrom, and third and fourth integrators for receiving the third and fourth product signals, respectively, and providing signals indicative of temperature at the sensor.

In some embodiments, (e.g., as illustrated in FIGS. 4 and 5), illuminators 425 and detectors 427 are integral elements of patch 420. In some embodiment, one portion of the interrogator may be included in the delivery device, while the other portion is implanted separately from but adjacent to the sensor. For example, the detector may be associated with the patch, and the illuminator portion may be implanted adjacent to the sensor; however, the positions may be reversed, with the detector adjacent to the sensor and the illuminator associated with the patch. Alternatively, neither the illuminator nor the detector may be associated with the patch. The invention admits variation in the configuration of the components.

A controller, not shown, may also be associated with patch 420. The controller receives signals from the interrogator, performs signal analysis, and calculates the analyte concentration.

Patch 420 may include an array of microneedles or tissue response modifier-eluting channels. Alternatively, patch 420 may comprise a transdermal delivery preparation such as a cream, a gel, or an ointment that includes tissue response modifier 422. As noted above, microneedles and transdermal delivery preparations may also serve as stand-alone delivery means.

Patch 420 is intended to be disposable. It includes sufficient tissue response modifier to last for a specified application period. Once the tissue response modifier is depleted, the user is alerted via instructions or an included signal to change the patch. Multiple patches may be required to achieve long-term use of the implant.

Implants Having Tissue-Integrating Electronic Apparatuses

Referring to FIG. 6A-14B, tissue-integrating electronic apparatuses (e.g., tissue-integrating opto-electronic apparatuses 500 and 600 and tissue-integrating electrochemical apparatuses 800 and 900) for detecting one or more analytes are illustrated according to embodiments of the invention. In the embodiments, the apparatuses are implanted in a mammalian body and are used to detect at least one analyte concentration from an in vivo sample (e.g., tissue).

The tissue-integrating electronic apparatuses include a tissue-integrating scaffold 502. In some embodiments, illustrated, for example, in FIG. 7A, the tissue-integrating scaffold 502 includes one or more flexible wires 504 embedded in or surrounded by a polymeric material 506. In another exemplary embodiment shown in FIG. 7B, the tissue-integrating scaffold 502 includes one or more layers of a conductive fabric or mesh material having one or more flexible wires 504 (or conductive threads) woven throughout the fabric. The conductive fabric (or e-textile) may be coated with the polymeric material 506. E-textiles, also known as electronic textiles, smart textiles, or smart fabrics, are fabrics that enable digital components (including small computers), and electronics to be embedded in them. Many intelligent clothing, smart clothing, wearable technology, and wearable computing projects involve the use of e-textiles.

The flexible wires 504 (see e.g., FIGS. 7A-9, 12A and 12B) are conductive and operatively couple or connect a sensor embedded in the scaffold 502 to a power source and/or control circuitry. The flexible wires 504 include coils, bends or angles such that the wires may stretch and twist with movement of the implanted apparatuses within the tissue of a subject. The flexible wires 504 also prevent breakage of the connection between the sensor and the power supply as well as the electrical control circuit. The diameter of each of the flexible wires 504 is typically about 1 nanometer to about 1 micrometer The flexible wires 504 may be formed of one or more conductive materials including, but not limited to, Au, Pd, Pt, Ag, Cu, Al, aluminum alloys, Ni, Zn, carbon, titanium, Cr, W, doped amorphous or polycrystalline silicon, Mo, Ta, carbon, conductive polymers, aligned tissue, and combinations thereof. Exemplary conductive polymers include polyacetylene, polypyrrole, polyaniline and copolymers thereof. Other examples of conductive polymers include poly(p-phenylene vinylene) and its soluble derivatives. Examples of aligned tissue (e.g., "biowires") include neurons or heart cells that conduct electricity and that are grown on suture material. Exemplary suture materials on which to grow cells include plain catgut, chromic catgut, polyglycolide and/or polydioxanone.

In embodiments in which the scaffold 502 is a conductive fabric, the conductive fabric may include a non-conductive or less conductive material such as, but not limited to, cotton, polyester, nylon, stainless steel, aramids, poly(p-phenylene-2,6-benzobisoxazole) and combinations thereof.

The tissue-integrating scaffold 502 may be constructed with materials and/or micro-architecture such that the scaffold 502 promotes tissue-integration and/or vascularization, as described in U.S. patent application Ser. No. 13/267,741 which is incorporated herein by reference in its entirety. For example, scaffolds 502 with one or more pores 505 (e.g., shown as voids in FIGS. 7A-9, 12A and 12B) provide tissue biomaterial anchoring and promote in-growth throughout the pores 505. The resulting "hallway" or "channel" pattern of tissue growth are healthy, space-filling masses that persist over time and promote host cell integration. In certain embodiments, the pore diameter may be from about 1 micron to about 1000 microns. Most or all of the pores 505 of the biomaterials described herein are preferably interconnected (co-continuous). The co-continuous pore structure of the biomaterials promotes space-filling in-growth of cells in the implant, which in turn limits the foreign body response and leads to long-term (greater than one week and up to years) persistence of the implant's ability to act as a sensor. The pores 505 may be uniform and/or irregular in shape. The pores 505 may be any shape, including spherical, cubic, polyhedral, ellipsoidal and/or cylindrical.

Alternative structures that provide tissue-integrating scaffolds include fibers (e.g., 1 to 10 or more microns in diameter, such as 5, 6, 7, 8, 9, 10 or more microns), which may be arranged in non-random or random configuration. The polymeric material 506 of the tissue-integrating scaffolds (in any configuration) can also be formed by multiphoton polymerization techniques. Kaehr et al. (2008) *Proc. Nat'l. Acad. Sci. USA* 105(26): 8850-8854; Nielson et al. (2009) *Small* 1:120-125; Kasprzak, Doctoral Dissertation, Georgia Institute of Technology, May 2009.

The polymeric material 506 may be composed of multiple materials, such as an insulating polymer coating the wires and/or a biocompatible polymer coating that forms the body contacting surface of all the wires. In some embodiments, the polymeric material 506 of the tissue-integrating scaffold 502 may include any material, including but not limited to conductive polymers, synthetic polymers, naturally occurring substances, or mixtures thereof. Examples of conductive polymers include, but are not limited to, polyacetylene, polypyrrole, polyaniline and copolymers thereof. Other examples of conductive polymers include poly(p-phenylene vinylene) and its soluble derivatives. Examples of synthetic polymers include, but are not limited to, polyethylene glycol (PEG), 2-hydroxyethyl methacrylate (HEMA), silicone rubber, poly([epsilon]-caprolactone) dimethylacrylate, polysulfone, (poly)methy methacrylate (PMMA), soluble Teflon-AF, (poly)ethylenetetrapthalate (PET, Dacron), Nylon, polyvinyl alcohol, polyacrylamide, polyurethane, and mixtures thereof. Examples of naturally-occurring materials include, but are not limited to, fibrous or globular proteins, complex carbohydrates, glycosaminoglycans, extracellular matrix, or mixtures thereof. Thus, the polymer material of the scaffold 502 may include collagens of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, chitosan etc. Natural polymers may be used as the scaffold or as an additive.

In some embodiments, the polymeric material 506 of the tissue-integrating scaffold 502 comprises a hydrogel. For example, the polymeric material 506 may comprise a hydrogel, for example by reacting hydroxyethyl methacrylate (HEMA), poly (hydroxyethyl methacrylate), pHEMA. Furthermore, various comonomers can be used in combination to alter the hydrophilicity, mechanical and swelling properties of the hydrogel (e.g. PEG, NVP, MAA). Non-limiting examples of polymers include 2-Hydroxyethyl methacrylate, polyacrylamide, N-vinylpyrrolidone, N,N-Dimethylacrylamide, poly(ethylene glycol) monomethacrylate (of varying molecular weights), diethylene glycol methacrylate, N-(2-hydroxypropyl)methacrylamide, glycerol monomethacrylate, 2,3-dihydroxypropyl methacrylate and combinations thereof. Non-limiting examples of cross-linkers include tetraethylene glycol dimethacrylate, poly(ethylene glycol) (n) diacrylate (of varying molecular weights), ethoxylated trimethylolpropane triacrylate, bisacrylamide and combinations thereof. Non-limiting examples of initiators include irgacure Series (UV), Azobisisobutyronitrile (AIBN) (thermal), Ammonium Persulfate (APS) (thermal).

The polymeric material 506 may be a sphere-templated hydrogel, for instance an inverse colloid crystal, for example as described in U.S. Pat. No. 7,972,628 to Ratner, et al. or other tissue-integrating materials.

The polymeric material 506 may be degradable, either by the body (biodegradable) or by the application of an external initiator to start or speed up the degradation process (e.g. UV, ultrasonics, radio frequency, or other exogenous sources to initiate degradation.). For example, the polymeric material 506 may include any biodegradable or bioresorbable polymers, including but not limited to degradable forms of alginates, poly(lactic acid), poly(vinyl alcohol), polyanhydrides, poly(glycolic acid), microporous polyesters, microporous polyethers and cross-linked collagen. One specific example is UV-photopolymerization of poly(ethylene glycol)-diacrylate and acrylated protease-degradable peptides and VEGF as described by Phelps, et al (2010) *Proc. Nat'l. Acad. Sci. USA* 107(8):3323-3328.

Other specific examples are polymers described by Kloxin et al. (2009) *Science* 324:59-63 and U.S. Pat. No. 6,013,122 whose degradation is controlled through exposure to exogenous energy forms as well as Alexeev et al. (2003) *Anal. Chem.* 75:2316-2323; Badylak et al. (2008) *Seminars in Immunology* 20:109-116; Bridges et al. (2010) 94(1):252-258; Isenhath et al. (2007) *Research* 83A:915-922; Marshall et al. (2004) *Polymer Preprints, American Chemical Society, Division of Polymer Chemistry* 45:100-101; Phelps et al. (2010) *Proc Nat'l Acad Sci USA.* 107(8):3323-8; Ostendorf and Chichkov (2006) *Two Photon Polymerization: A New Approach to MicroMachining, Photonics Spectra*; Ozdemir et al. (2005) *Experimental and Clinical Research, Plast. Reconstr. Surg.* 115:183; U.S. Patent Publication No. 20080075752; Sanders et al. (2003) *Journal of Biomedical Materials Research* Part A 67A(4):1181-1187; Sanders et al. (2002) *Journal of Biomedical Materials Research* 62(2): 222-227; Sanders et al. (2003) *Journal of Biomedical Materials Research* 65(4):462-467; Sanders et al. (2005)*Biomaterials* 26:813-818; Sanders et al. (2005) *Journal of Biomedical Materials Research* Part A 72(3):335-342; Sanders (2003) *Journal of Biomedical Materials Research* 67(4): 1412-1416; Sanders et al. (2000) *Journal of Biomedical Materials Research* 52(1):231-237; and Young Min Ju et al. (2008) *J Biomed Mater Res* 87A:136-146.

In certain embodiments, the tissue-integrating scaffold 502 of the invention is constructed such that tissue response modifiers are released from the polymeric material 506 to promote or enhance tissue-integration and vascularization.

In addition, the tissue-integrating scaffold 502 of the invention may be constructed such that it has conduits, pores or pockets that are hollow or filled with degradable, angiogenic, or other substances (e.g. stem cells). As noted above, once in the body, the biodegradation of the material filling the conduits, pores or pockets, creates space for tissue, including capillaries to integrate with the material. The degradable material that initially fills the conduits, pores or pockets may enhance vessel growth or tissue growth within the scaffold. This architecture promotes new vessel formation and maintains healthy viable tissue within and around the implant.

The tissue-integrating scaffold 502 of the invention may be constructed such that it is permeable to analytes of interest (e.g., glucose can diffuse into a tissue-integrating conductive hydrogel scaffold and reach the sensing moieties that are embedded within the hydrogel matrix).

In some embodiments, the tissue integrating apparatuses include one or more sensors such as, but not limited to, a light source 508, a detector 510, a temperature sensor 511, a pressure sensor 512, an accelerometer 513, a piezoelectric sensor, an electrochemical sensor (i.e., an electrode) and combinations thereof. The sensors may be sized such that they are tissue integrating or tissue anchoring. In some embodiments, the tissue integrating sensors are about 10 to 100 microns in at least one dimension. In other embodiments, the tissue anchoring sensors are about 100 microns or more in at least one dimension.

In some embodiments, the tissue anchoring sensors include a plurality of holes or perforations to promote collagen and tissue in-growth. The plurality of holes or perforations typically are at least 1 micron in one dimension. In certain embodiments, the tissue anchoring sensors include a porous coating of polymeric material 506 as described previously. In some embodiments, the tissue anchoring sensors include a textured coating with one or more projections that promote collagen and tissue in-growth. Textured coatings may be formed with biocompatible polymeric materials 506 as described previously. In some embodiments, the tissue anchoring sensors include pillars formed from silicon rubber. In some embodiments, Velcro-like or velour-like coatings formed from PET (Dacron). In some embodiments, the tissue anchoring sensors include a textured or roughened surface formed by laser and/or chemical etching of the sensor surfaces that are in contact with tissue. In some embodiments, a mold with texturizing features is used during a molding process of the sensor housing or substrate to introduce one or more textured surfaces to the sensor.

The sensor may be of such a size that the sensor partially or totally fills one or more pores 505 within the tissue-integrating scaffold 502. In some embodiments, the sensor is the same size as or at least 1.5 times larger than the diameter of a pore within the tissue-integrating scaffold 502.

Examples of temperature sensors include, but are not limited to, one or more CMOS-based microchip temperature sensors, thermocouples, thermistors or combinations thereof. Temperature sensors may be used to correct an analyte concentration measured from an in vivo sample.

A. Tissue-Integrating Opto-Electronic Apparatuses

Figure 8B:
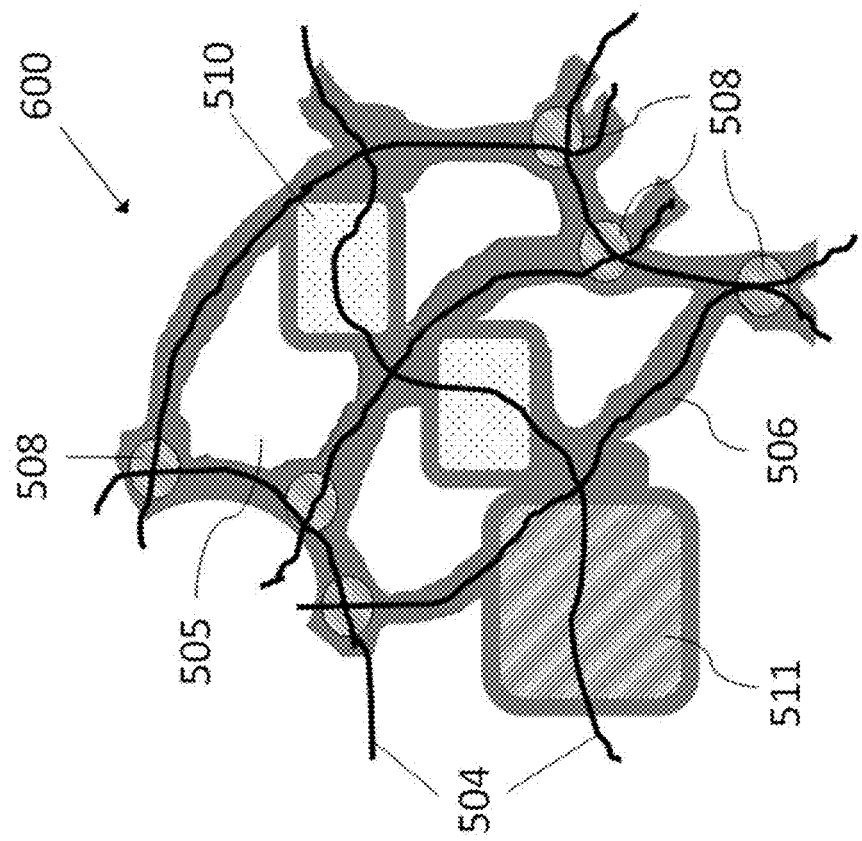
FIG. 8B is a simplified cross-sectional view of an example of a tissue-integrating electronic apparatus as shown in FIG. 6B in which the apparatus is a tissue-integrating opto-electronic apparatus having a scaffold coated with a polymeric material, according to an embodiment.
Figure 8A:
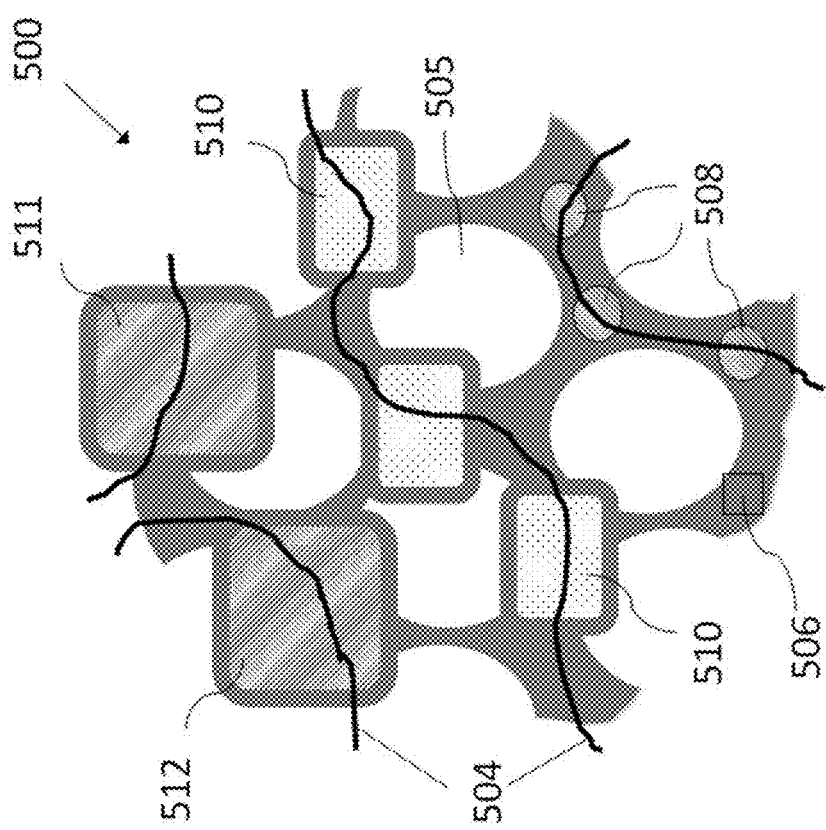
FIG. 8A is a simplified cross-sectional view of an example of a tissue-integrating electronic apparatus as shown in FIG. 6A in which the apparatus is a tissue-integrating opto-electronic apparatus having a scaffold coated with a polymeric material, according to an embodiment.

Referring to FIGS. 8A-12B, various views of embodiments of tissue-integrating opto-electronic apparatuses 500 and 600 are illustrated. FIG. 8A illustrates a tissue-integrating opto-electronic apparatus 500 in which the scaffold 502 includes one or more conductive flexible wires 504 embedded in a polymeric material 506 as described. FIG. 8B illustrates a tissue-integrating opto-electronic apparatus 600 in which the scaffold 502 includes one or more conductive flexible wires 504 woven throughout a fabric or mesh material, all of which is coated with a polymeric material 506 as described. In addition to the tissue-integrating scaffold 502, the tissue-integrating opto-electronic apparatuses 500 and 600 include a plurality of tissue-integrating sensors (i.e., at least one light source 508 and at least one detector 510) and one or more sensing moieties 514 (shown in FIG. 10). The light source 508 emits light and the one or more sensing moieties 514 produce a detectable signal in the presence of the analyte.

Figure 10B:
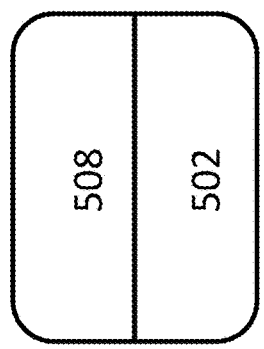
FIGS. 10A-10D are schematics of examples of a tissue-integrating opto-electronic apparatus, according to embodiments.
Figure 10D:
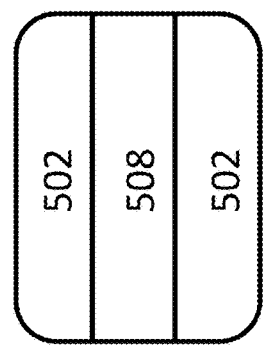
Figure 10A:
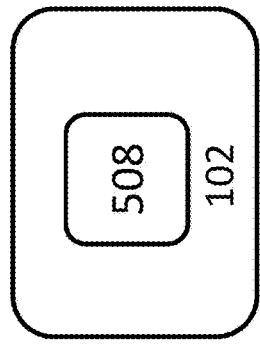
Figure 10C:
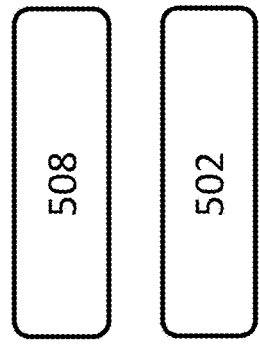
Figure 19:
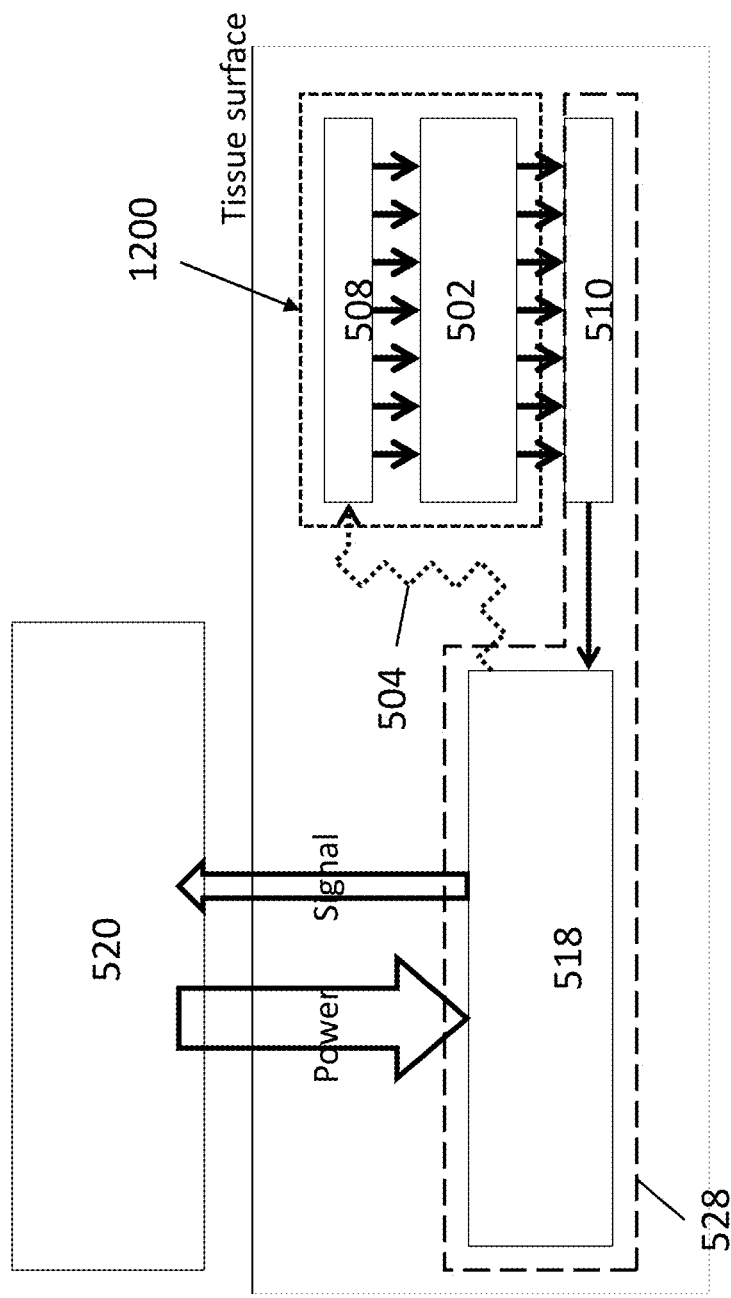
FIG. 19 is a schematic top view of an example of a system having a tissue integrating opto-electronic apparatus in which a light source is integrated with a scaffold, according to an embodiment. The system also includes an implantable tissue anchoring module and an external module. The implantable module is proximate (e.g., located at a distance of about 1 millimeter or less away from) the opto-electronic apparatus and is operatively coupled to a flexible wire in the opto-electronic apparatus.

The light source 508 emits light in the near infrared wavelength range of 600 nanometers to 900 nanometers. In some embodiments, e.g., as illustrated in FIGS. 8A, 8B and 3, the tissue-integrating light source 508 is integrated with the tissue-integrating scaffold 502 such that the light emitted from the light source 508 is efficiently transferred to the one or more sensing moieties 514. In some embodiments, e.g., as illustrated in FIGS. 10A, 18A and 18B, the tissue-integrating light source 508 may be embedded in or surrounded by the tissue-integrating scaffold 502 having one or more sensing moieties 514. In some embodiments, e.g., as illustrated in FIGS. 10B and 19, the light source 508 is adjacent to (e.g., located at a distance of about 100 microns or less away from) the tissue-integrating scaffold 502 having one or more sensing moieties 514. In some embodiments, e.g., as illustrated in 10C, 20A and 20B, the light source 508 is proximate (e.g., located at a distance of about 1 millimeter or less away from) the tissue-integrating scaffold 502 having one or more sensing moieties 514. In some embodiments, e.g., as shown in FIG. 10D, the light source 508 is sandwiched between layers of the tissue-integrating scaffold 502.

In some embodiments, the light source 508 is one or more light emitting diodes (LEDs), e.g., a multi-wavelength LED array. In some embodiments, the light sources 508 are one or more micro LEDs. In an embodiment in which the light sources 508 are one or more micro LEDs, each micro LED is about 0.1 micrometers to about 6 micrometers in size.

Typical materials from which the micro LEDs are formed may include, but are not limited to, indium arsenide-based nanocrystals, gallium nitride, indium gallium arsenide, gallium arsenide, aluminum gallium arsenide, gallium arsenide phosphide, aluminum gallium indium phosphide, gallium (III) phosphide, organic polymers such as poly (9-vinylcarbazole) (PVK) doped with an electron-transport material (e.g., 2-(4-biphenylyl)-5-(4-tert-butylphenyl)-1,3,4-oxadiazole) and a near-IR-emitting molecule (e.g., 2-(6-(p-dimethylaminophenyl)-2,4-neopentylene-1,3,5-hexatrienyl)-3-ethylbenzothiazolium perchlorate), and combinations thereof.

The light source 508 may be connected in series or in parallel by the one or more conductive flexible wires 504 to a power source and/or a control circuit.

Figure 11:
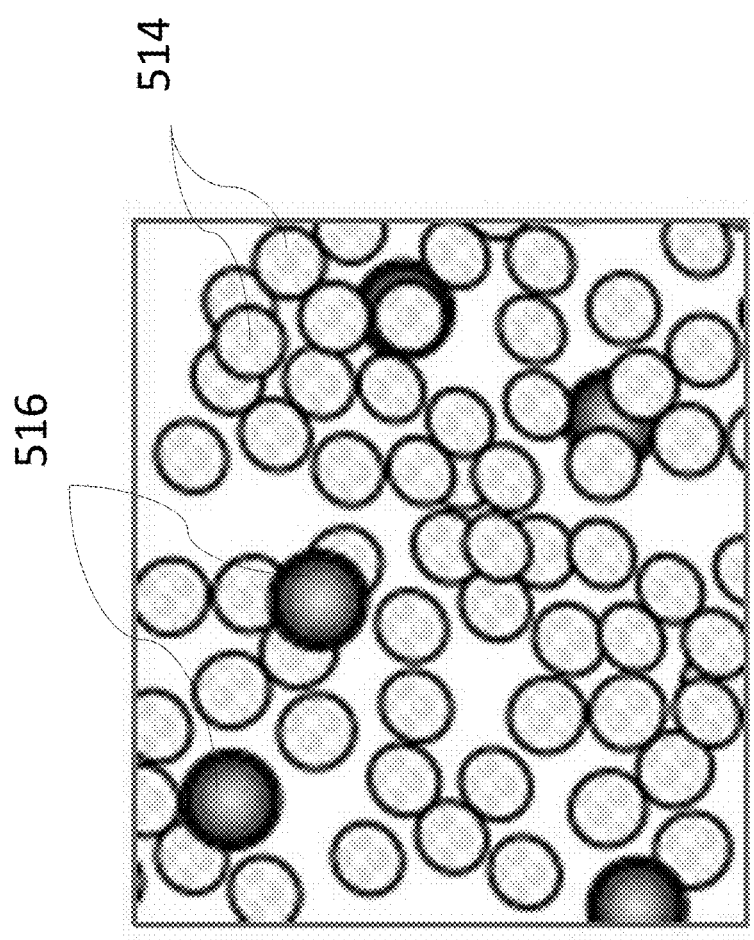
FIG. 11 is a simplified cross-sectional view (boxed area of FIG. 6A) of an example of a tissue-integrating opto-electronic apparatus having sensing moieties embedded within a polymeric material of the scaffold, according to an embodiment.

Referring to FIG. 11, a cross sectional view the polymeric material 506 of the tissue-integrating scaffolds 502 is illustrated (e.g., boxed area of FIG. 8A). The polymeric material 506 described herein can be combined with (or made up of) one or more sensing moieties 514 that produce a detectable signal in the presence of one or more analytes, as described in the aforementioned U.S. patent application Ser. No. 13/267,741 which is incorporated herein by reference in its entirety.

Non-limiting examples of analytes that may be detected by an apparatus having the sensing moieties 514 include oxygen, reactive oxygen species, glucose, lactate, pyruvate, cortisol, creatinine, urea, sodium, magnesium, calcium, potassium, vasopressin, hormones (e.g., Luteinizing hormone), pH, cytokines, chemokines, eicosanoids, insulin, leptins, small molecule drugs, ethanol, myoglobin, nucleic acids (RNAs, DNAs), fragments, polypeptides, single amino acids and the like.

Any suitable moiety can be used to sense the analyte of interest, including but not limited to analyte binding molecules (e.g. glucose binding proteins), competitive binding molecules (e.g. phenylboronic acid based chemistries), analyte specific enzymes (e.g. glucose oxidase), ion sensitive materials, or other analyte sensitive molecules (e.g. oxygen sensitive dyes such as porphyrins). The sensing moieties 514 may be in any form, for example, microspheres, nanospheres, fibers, etc. A single implant (tissue-integrating scaffold) typically includes a plurality of sensing moieties 514. In certain embodiments, the sensing moieties 514 are all the same while in other embodiments, a mixture of two or more sensing moieties is used.

To enhance or create a detectable signal, sensing molecules may be labeled with a reporter (e.g., one or more fluorophores, one or more gold particles, one or more quantum dots and/or one or more single-walled carbon nanotubes). Sensing molecules may also create a signal through swelling, optical diffraction, change in absorbance FRET, quenching.

Non-limiting examples of suitable sensing molecules include but are not limited to dye labeled Concanavalin A with glycodendrimer or dextran (see, e.g., Ballerstedt et al. (1997) *Anal. Chim. Acta* 345:203-212) and alcohol sensitive oxo-bacteriochlorin derivative fluorescent binding protein developed by Takano, et al (2010) *The Analyst* 135:2334-2339 as well as Vladimir et al. (2004) *Clinical Chemistry* 50:2353-2360; Aslan et al. (2005) *Chem.* 1; 77(7):2007-14; Ballerstadt et al. (1997) *Anal. Chim. Acta* 345:203-212 (1997); Billingsley et al. (2010) *Anal. Chem.* 82(9):3707-3713; Brasuel et al. (2001) *Anal. Chem.* 73(10):2221-2228; Brasuel, et al. (2003) *The Analyst* 128(10):1262-1267; Horgan et al. (2006) *Biosensors and Bioelectronics* 211838-1845; Ibey et al. (2005) *Anal Chem* 77:7039-7046; Nielsen et al. (2009) *Journal of Diabetes Science and Technology* 3(1):98-109; McShane et al. (2000) *IEEE Engineering in Medicine and Biology Magazine* 19:36-45; Mansouri & Schultz (1984) *Bio/Technology* 23:885-890; Rounds, et al. (2007) *Journal of Fluorescence* 17(1):57-63; Russell et al. (1999) *Analytical Chemistry* 71(15):3126-3132; Schultz et al. (1982) *Diabetes Care* 5:245-253; Srivastava, & McShane (2005) *Journal of Microencapsulation* 22(4):397-411; Srivastava et al. (2005) *Biotechnology and Bioengineering* 91(1):124-131; Takano et al. (2010) *The Analyst* 135:2334-2339.

The sensing moiety 514 may comprise other molecules besides sensing molecules, such as carrier molecules/polymers (e.g. the sensing moiety element may comprise PEG nanospheres, alginate particles or other carrier materials that contain sensing molecules). The sensing moiety 514 may also contain one or more reference molecules 516 or stabilizing molecules that do not sense any analytes, but that serves as calibrators or stabilizers. Examples of calibrators include, but are not limited to, a reference dye or any substance that provides a stable reference signal (e.g., optical, magnetic, electrochemical, electrical, temperature, pressure, ultrasound, acoustic, radiation) to which the signal modulated by the analyte of interest may be compared for calibration. Examples of stabilizers include, but are not limited to, catalayse and/or any free-radical scavenger, which helps preserve the sensing moieties or other stabilizer.

The sensing moiety 514 may be thermally responsive material, pressure-responsive material or materials that swell, shrink, change optical properties, or change other measurable properties in response to a stimulus.

The analyte sensing moieties 514 may be combined with the polymeric material 506 of the tissue-integrating scaffolds 502 in a variety of ways to produce tissue-integrating opto-electronic apparatuses 500 and 600. In some embodiments, the sensing moieties 514 are physically entrapped or chemically bound within the scaffold 502. In other embodiments, the sensing moieties 514 are attached directly (e.g., via covalent or noncovalent linkages) to the surface of the tissue-integrating scaffold 502 and may optionally be covered by an exterior coating. The purpose of the exterior coating is, for example, to hold the sensing moieties in place, to protect the sensing moieties from external forces, to limit/impede diffusion of various molecules and/or to provide a desired exterior surface, and to transduce the sensing signal from the chemistry to the scaffold and/or external detector.

In some embodiments the tissue-integrating scaffold 502 itself is composed of sensing moieties where the sensing moieties are in the form of particles (spherical or other shapes) that are bonded together (e.g. chemically, thermally, pressure, etc.) or where the polymer itself provides the sensing capability (e.g. stimuli-sensitive polymers).

In some embodiments, the tissue-integrating scaffold 502 is composed of distinct layers where sensing moieties 514 are physically entrapped or chemically bound to or within specific layers of the scaffold 502, and other layers provide other features such as mechanical strength, elasticity, conductivity or other properties.

In some embodiments, the tissue-integrating scaffold 502 is composed of a polymer that swells or shrinks in response to a stimulus (e.g. concentration of an analyte of interest, temperature, or other stimuli). The shrinking or swelling may cause optical change (e.g. due to light diffraction, change in distances between gold nanoparticles contained within the matrix, or other interaction (Aleexev et al and Aslan, et al)).

Table 1 below provides a matrix showing how sensing moieties can be combined with tissue-integrating scaffolds in a variety of ways to tissue-integrating sensing media.

TABLE 1

Sensing Media/Scaffold Matrix

| | Sensing Moieties | | | |
|---|---|---|---|---|
| Tissue-integrating Scaffolds | Sensing particles (e.g. PEG microspheres containing ConA with glycodendrimer, alginate nanospheres containing ApoGox with reported dye.) | Sensing chemistry (e.g. boronic acid based chemistry, sensing chemistry attached to quantum dots or gold nano-rods) | Any other fluorescent sensing assay (e.g. glucose oxidase with porphyrin dye) | Stimuli responsive moieties (temperature, pressure, other) |
| Permeable Biomaterial Scaffold (e.g. hydrogel ICC) (Kotov, Marshall) Non-Permeable Scaffold (ICC) (e.g. Porex, MedPor) Naturally derived scaffolds (e.g. fibrin, BSA, collagen synthetic or decellularized ECM (sECM), Prestwich, Badylak, Taylor, Small fibers (Sanders) | Polymerization (SM contained within mesh of scaffold polymer) Immobilization (conjugation or physical entrapment) of SM on surface Making scaffold of sensing moiety Immobilization of SM on surface Physical entrapment of SM on surface SM contained within mesh of naturally derived matrix Immobilization of SM on surface Physical entrapment of SM on surface Polymerization (SM trapped IN fiber matrix) Immobilization (conjugation or physical entrapment) of SM on surface Making scaffold of sensing moiety Multi-layer fibers (e.g. sensing layer, biocompatibility layer, stabilizing or structural layer, voids or cellular conduits | Polymerization (SM contained within mesh of scaffold polymer) Immobilization (conjugation or physical entrapment) of SM on surface Making scaffold of sensing moiety Immobilization of SM on surface Physical entrapment of SM on surface SM contained within mesh naturally derived matrix) Immobilization of SM on surface Physical entrapment of SM on surface Polymerization (SM trapped IN fiber matrix) Immobilization (conjugation or physical entrapment) of SM on surface Making scaffold of sensing moiety Multi-layer fibers (e.g. sensing layer, biocompatibility layer, stabilizing or structural layer, voids or cellular conduits | Polymerization (SM contained within mesh of scaffold polymer) Immobilization (conjugation or physical entrapment) of SM on surface Making scaffold of sensing moiety Immobilization of SM on Surface Physical entrapment of SM on surface SM contained within mesh of naturally derived matrix) Immobilization of SM on surface Physical entrapment of SM on surface Polymerization (SM trapped IN fiber matrix) Immobilization (conjugation or physical entrapment) of SM on surface Making scaffold of sensing moiety Multi-layer fibers (e.g. sensing layer, biocompatibility layer, stabilizing or structural layer, voids or cellular conduits | Polymerization (SM contained within mesh of scaffold polymer) Immobilization (conjugation or physical entrapment) of SM on surface Making scaffold of sensing moiety Immobilization of SM on surface Physical entrapment of SM on surface SM contained within mesh of naturally derived matrix Immobilization of SM on surface Physical entrapment of SM on surface Polymerization (SM trapped IN fiber matrix) Immobilization (conjugation or physical entrapment) of SM on surface Making scaffold of sensing moiety Multi-layer fibers (e.g. sensing layer, biocompatibility layer, stabilizing or structural layer, voids or cellular conduits |

In some embodiments, the apparatuses 500 and 600 further comprise additional moieties (e.g., non-sensing or additional sensing moieties different from the sensing moieties), for example reference (or calibration) moieties 516 (see FIG. 11). Reference or calibration moieties 516 include, but are not limited to, dyes, fluorescent particles, lanthanides, nanoparticles, microspheres, quantum dots or other additives or elements of the implant whose signal does not change due to the presences of the analyte (e.g., glucose). See, e.g., Chaudhary et al. (2009) *Biotechnology and Bioengineering* 104(6):1075-1085. Fluctuations in the reference (calibration) signal(s) can be used to correct or calibrate the sensing signal(s). Reference signals might fluctuate due to changes in the amount of light reaching the implant (ambient light changes, fluctuating LED or laser source). Sensing signals would also be subject to fluctuations in the amount of light reaching the implant; however it is desirable that the signal of interest only fluctuates based on analyte (e.g., glucose) fluctuations. Therefore the reference signal is used to correct or calibrate the sensing signal when it fluctuates due to influences other than changes in glucose concentration. Reference signals might also fluctuate due to changes in the reference moiety itself (e.g. photodegradation, chemical degradation). The sensing signal(s) would have the same degradation or a rate of degradation that is relatable to the reference to allow for correction or calibration by the reference. Reference signals might also fluctuate due to physiological fluctuations that alter the light propagation through tissue (e.g. dehydration, oxygenation, blood flow). Sensing signals would be affected in the same way or in a way that is relatable to the reference fluctuations thereby permitting correction or calibration of the sensing signal by the one or more references. Thus, the sensing signal can be calibrated by reference to the signal(s) obtained from the calibration (reference) moieties.

In some embodiments, the sensing moieties 514 produce a detectable signal in the presence of glucose and the reference moiety comprises a molecule that measures (produces a detectable signal in the presence of) oxygen ($O_2$). As noted above, the sensing moieties can include an enzyme, for example glucose oxidase, which is specific for the substrate glucose. The reaction of glucose oxidase causes the substrate glucose to be converted to D-glucono-1,5-lactone, which then hydrolyzes to gluconic acid. Oxygen is consumed and converted to $H_2O_2$. The reduction of $O_2$ in the vicinity of the enzyme can be measured by using an $O_2$-sensitive fluorescent dye, such as a porphyrin dye. These dye molecules are quenched in the presence of $O_2$, so the reduction of $O_2$ by the action of GOx, causes an increase in fluorescence. The amount of fluorescence emitted from the $O_2$ calibration moieties is thus proportional to the concentration of glucose in the sensor.

The concentration of $O_2$ in the tissue can also vary physiologically, thereby changing or limiting the reaction of the enzyme in the sensing moieties. Therefore, the $O_2$ concentration in the sensor can be measured independent of the glucose concentration. Such a reference measurement of $O_2$ would allow corrections to be made to the glucose-specific signal from the sensing moieties.

In some embodiments, an analyte-specific enzyme that causes a change in pH would require the use of a separate pH-sensitive fluorescent dye with an emission spectral peak different and distinguishable from the analyte-specific dye reporting on the activity of the analyte-specific enzyme, for example when the sensing moieties comprise, urease used for measuring urea.

In other embodiments, the sensing moieties 514 comprise a first fluorescent dye and the reference molecule 516 comprises a second (different) fluorescent dye. As noted above, the sensing moieties may utilize an analyte-specific chemistry that includes a ligand receptor moiety and an analyte analogue moiety. One of the binding members is labeled with a fluorescent dye and the other binding member is labeled with a dye that quenches the fluorescent dye when the analyte analogue moiety binds to the ligand receptor moiety. Non-limiting examples include glycodendrimer, which binds to Concanavalin A, wherein the Concanavalin A is labeled with Alexafluor 647 and the glycodendrimer is labeled with QDY21 dark quencher. Concanavalin A binds to glucose and the glycodendrimer competes with glucose for the binding to Concanavalin A. The chemistry is immobilized as described in this invention within the tissue-integrating scaffold 502 and implanted into the dermis or subcutaneous tissue. To measure glucose in the tissue, the tissue-integrating scaffold 502 is illuminated from a patch reader on top of the skin above the implant with 650 nm light at desired intervals over the long-term life of the implant (e.g., every 5-60 minutes over a period of 90 days or more). The amount of fluorescent signal (e.g., from a molecule such as Alexafluor 647) detected is proportional to the concentration of glucose in the tissue. However, over the long-term life of the implants described herein, the dye can photobleach, i.e., the amount of fluorescent signal emitted back through the skin at a given glucose concentration is diminished. Thus, a reduction of fluorescence due to photobleaching can make it appear that analyte is at a lower concentration than it really is.

To correct for this effect, a separate internal photobleaching control is employed. In certain embodiments, the separate internal control is a second fluorescent dye, different from the fluorescent molecule included in the sensing moieties (e.g., Alexafluor 750 in the reference moieties when the sensing moieties comprise Alexafluor 647), which included immobilized in the scaffold 502. The fluorescence of reference moieties is not affected by the concentration of glucose, and both the first (e.g., Alexafluor 647) and second (e.g., Alexafluor 750) fluorescent dyes have predictable and well-characterized photobleaching rates. To control for the photobleaching of the dye of the sensing moieties, the fluorescence is measured for both dyes. The fluorescence value of the dye in the reference moieties can then be used to correct for any photobleaching of the dye in the sensing moieties.

In some embodiments, internal reference control materials can be employed that facilitate correcting for tissue optical variation. The electronic tissue-integrating implanted biosensor typically resides 3-4 mm under the surface of the scan. It is well known that in skin excitation light and emitted fluorescent light in the near infrared range are highly scattered as the light traverses the tissue between the reader patch and the implant. The extent of absorption and scattering is affected by physical properties such as temperature or by tissue composition, including but not limited to variations in blood perfusion, hydration, and melanin concentration. Skin variations can occur between users or between different time points for a single patient, and these variations can affect the fluorescence excitation and emissions signals causing in accurate signals for the analyte-specific signal. Accordingly, a separate fluorescence molecule with emission spectra distinguishable from the analyte-specific fluorescence can be immobilized into the scaffold 502. The fluorescence from the molecule can be measured separately from the analyte-specific fluorescence to measure a signal that informs about variations in tissue composition. The dye selected is based on having a similar response to tissue variations as the analyte-specific dye. Dyes such as Alexafluor 750, various quantum dots (QD's), or lanthanide dye nanocrystals all can provide this capability.

Referring again to FIGS. 8A, 8B, 19, 20A and 20B, the detector 510 of the tissue-integrating opto-electronic apparatuses 500-600 and 1100-1300 is configured to receive at least one detectable signal from the sensing moieties 514 and to output an electrical signal in response to the received signal.

In the embodiments illustrated in FIGS. 8A and 8B, the detector 510 is tissue integrating (i.e., is about 500 nanometers to about 100 microns in size) and is embedded within (or surrounded by) the tissue-integrating scaffold 502. In an embodiment, the detector 510 is one or more organic photodiodes. In an embodiment, the one or more organic photodiodes includes a near-IR absorbing layer formed from octabutoxy tin naphthalocyanine dichloride (OSnNcCl2).

Figure 9:
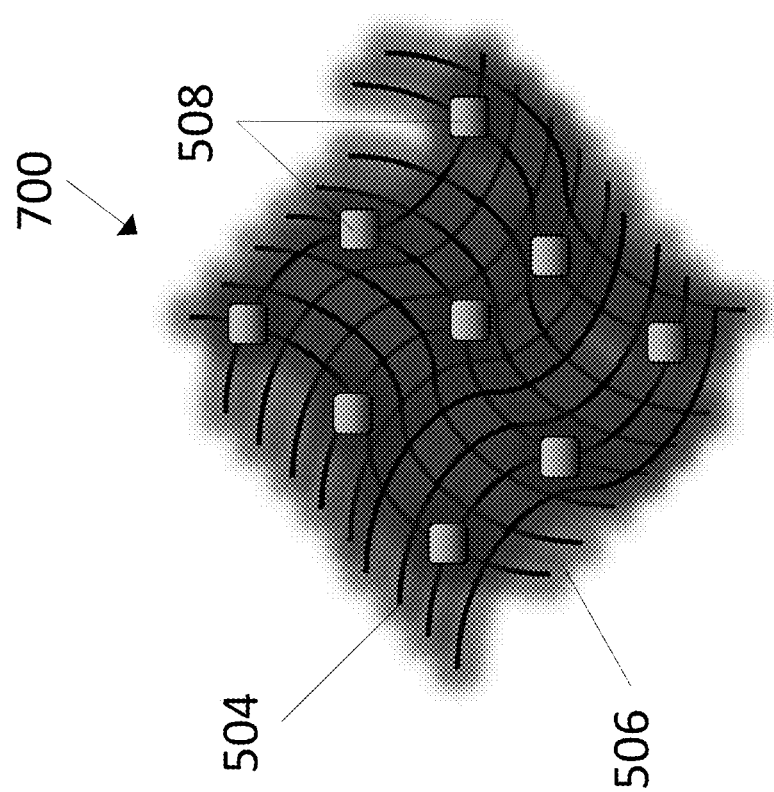
FIG. 9 is a perspective view of an example of a tissue-integrating opto-electronic apparatus in which one or more light sources are integrated with the scaffold, according to an embodiment.
Figure 17:
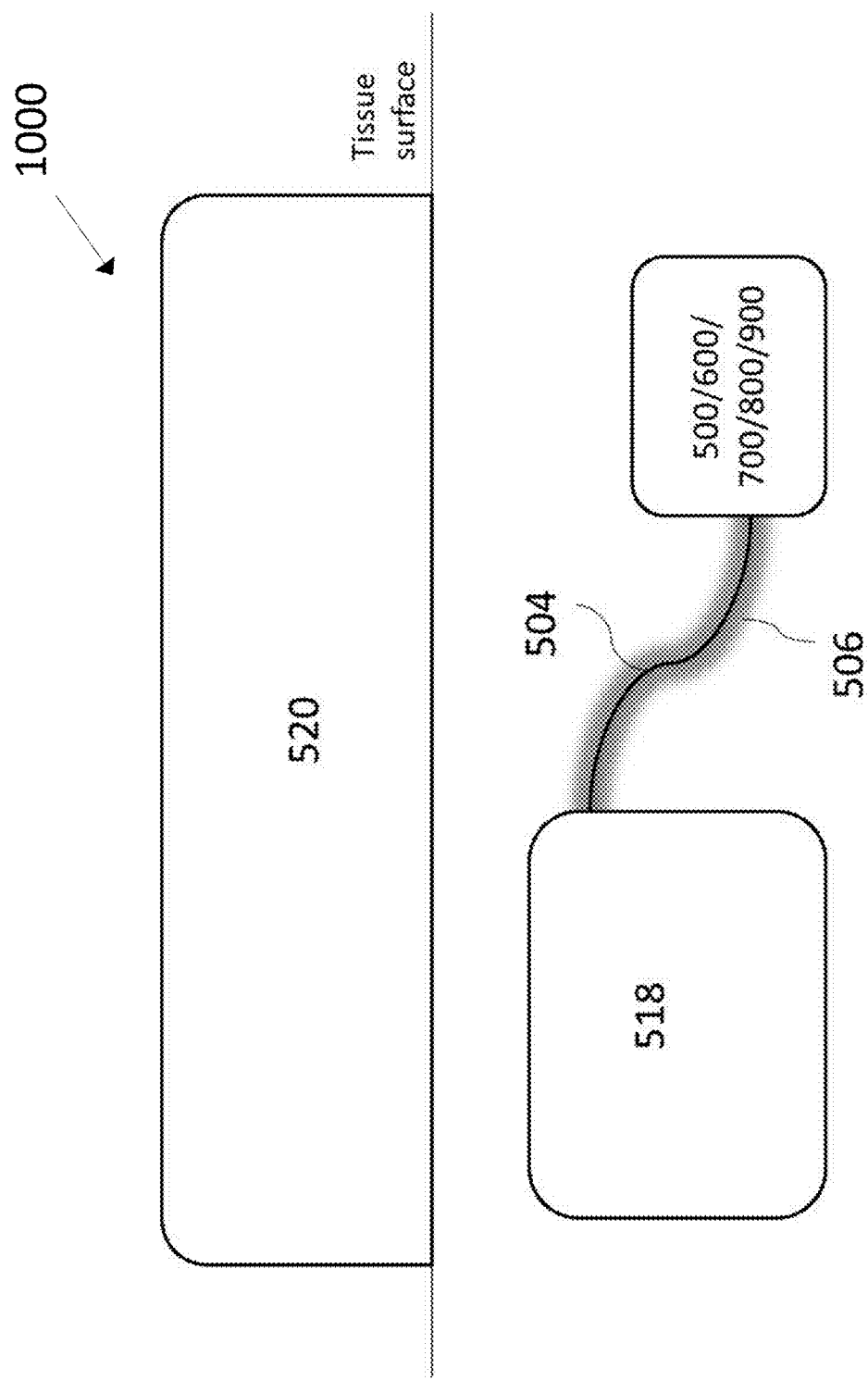
FIG. 17 is a schematic of an example of a system including one or more tissue-integrating electronic apparatuses, an implantable module and a non-implantable external device, according to an embodiment.
Figure 18:
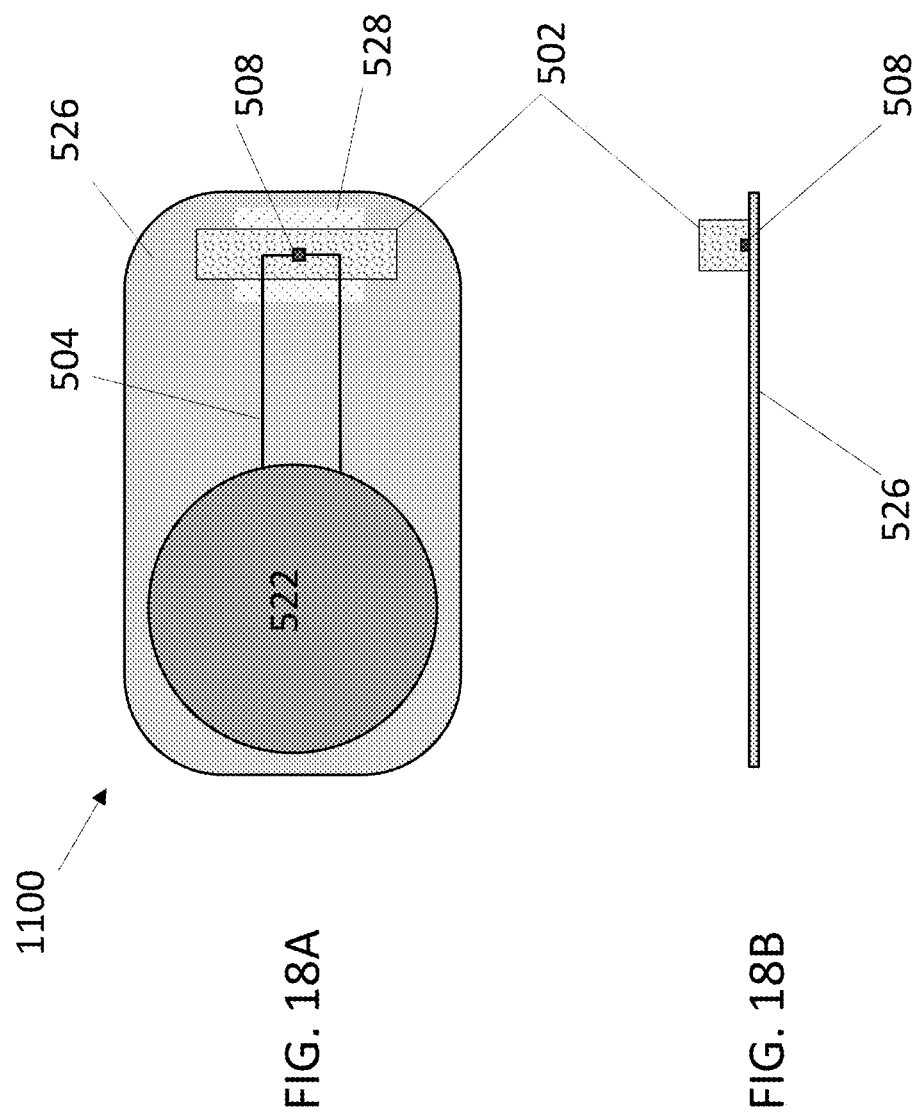
FIGS. 18A-18B are top and cross sectional schematic views of an example of a system having a tissue integrating opto-electronic apparatus in which a light source is integrated with a scaffold, according to an embodiment. The system also includes an implantable tissue anchoring module operatively coupled to the opto-electronic apparatus.

Unlike the embodiments shown in FIGS. 8A and 8B in which the implantable apparatus 500/600 includes a detector 510, opto-electronic apparatuses 700 and 1100 shown in FIGS. 9, 18A and 18B include a detector 510 located in an external device 520 (shown in FIG. 17).

In other embodiments of an opto-electronic apparatus 1200 illustrated in FIG. 19, one or more detectors 510 are proximate (e.g., located at a distance of about 1 millimeter or less away from) the tissue-integrating scaffold 502 and are associated with an implantable module 518. The detectors 510 are located such that they do not promote the foreign body response at a surface of the tissue-integrating scaffold 502. The location at which the detector 510 is placed can be chosen such that detection of one or more signals from the sensing moieties 514 is optimized and such that detection of light from the tissue-integrating light source 508 is minimized. In an opto-electronic apparatus 1300 illustrated in FIGS. 20A and 20B, the tissue-integrating scaffold 502 with sensing moieties 514 is sandwiched between one or more light sources 508 and one or more detectors 510. In this embodiment, the light sources 508 and the detectors 510 are proximate the tissue-integrating scaffold 502.

The detectors 510 illustrated in FIGS. 19-20B are sized such that one dimension is at least 500 nanometers (i.e., they may be tissue integrating or tissue anchoring, depending on the size). In some embodiments, the one or more detectors 510 are organic photodiodes. In some embodiments, the detector 510 is a multi-wavelength photodiode array having about a 50 micrometer to 2 millimeter square photosensitive area. Typical materials from which the photodiodes are formed include but are not limited to Si, InGaAS and combinations thereof. In some embodiments, the one or more detectors 510 are a CCD image sensor.

The detector 510 may include one or more filters to filter out stray light and/or light from the light source 508. The detectors 510 may be connected in series or in parallel by flexible wires 504 to a power source and/or electrical component control circuitry, as will be described.

B. Tissue-Integrating Electrochemical Apparatuses

Figure 12B:
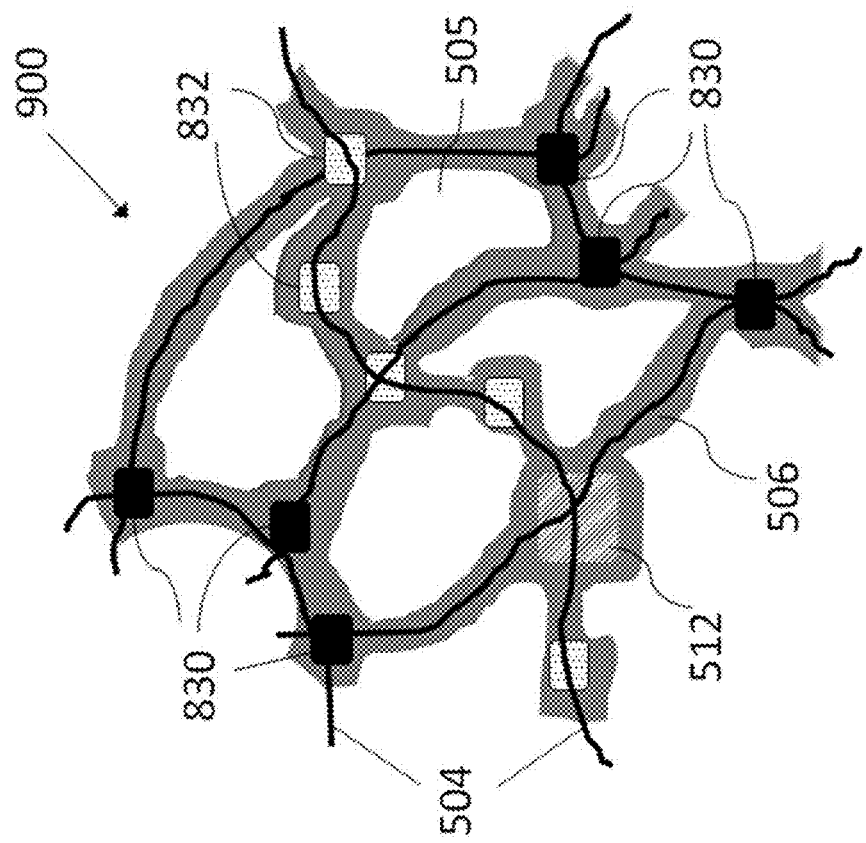
FIG. 12B is a simplified cross-sectional view of an example of a tissue-integrating electronic apparatus as shown in FIG. 6B in which the apparatus is a tissue-integrating electrochemical apparatus having a scaffold coated with a polymeric material, according to an embodiment.
Figure 12A:
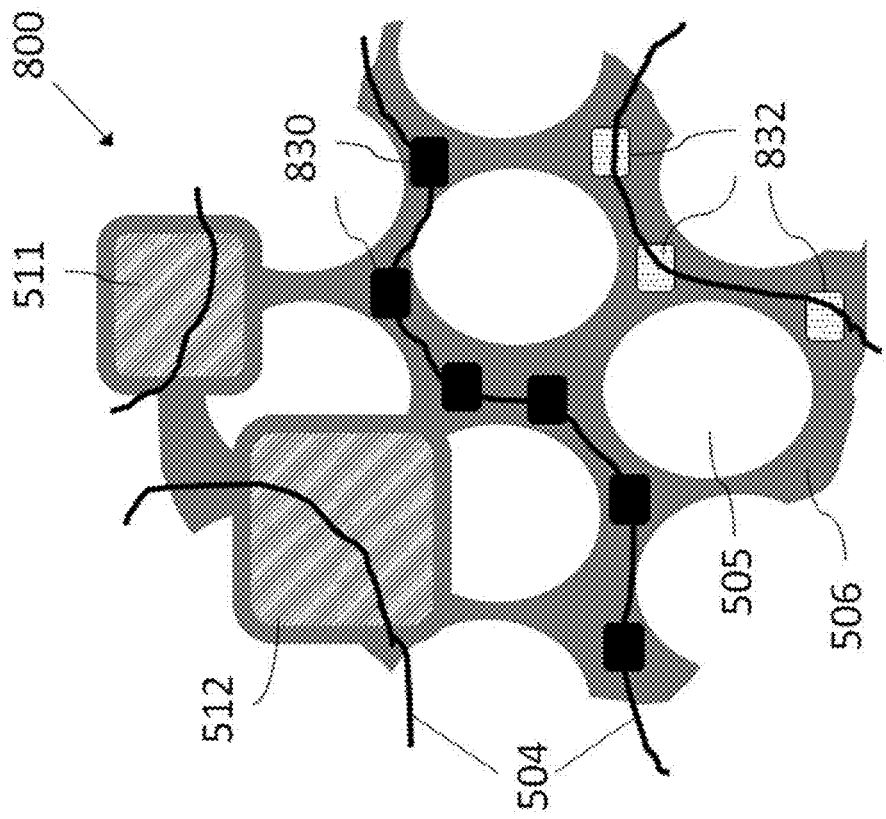
FIG. 12A is a simplified cross-sectional view of an example of a tissue-integrating electronic apparatus as shown in FIG. 6A in which the apparatus is a tissue-integrating electrochemical sensor having a scaffold coated with a polymeric material, according to an embodiment.

Referring to FIGS. 12A and 12B, cross sectional views of embodiments of tissue-integrating electrochemical apparatuses 800 and 900 are illustrated. FIG. 12A illustrates a tissue-integrating electrochemical apparatus 800 in which the scaffold 502 includes one or more flexible wires 504 embedded in a polymeric material 506 as described. FIG. 12B illustrates a tissue-integrating electrochemical apparatus 900 in which the scaffold 502 includes one or more flexible wires 504 woven throughout a fabric (e.g., e-textile) or mesh material all of which is coated with a polymeric material 506 as described. In addition to the tissue-integrating scaffold 502, the tissue-integrating electrochemical apparatuses 800 and 900 include one or more tissue-integrating electrodes (e.g., one or more working electrodes 830 and one or more reference/counter electrodes 832).

Figure 13B:
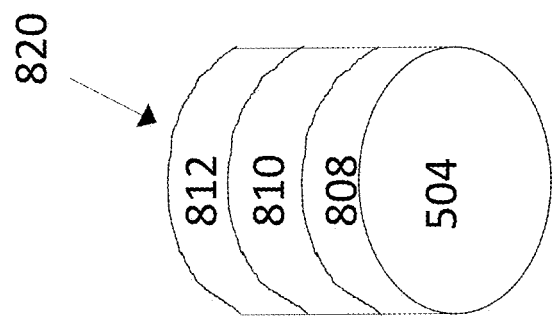
FIG. 13B is a cross-sectional view of an example of an electrode illustrated in FIG. 13A, according to an embodiment.
Figure 13A:
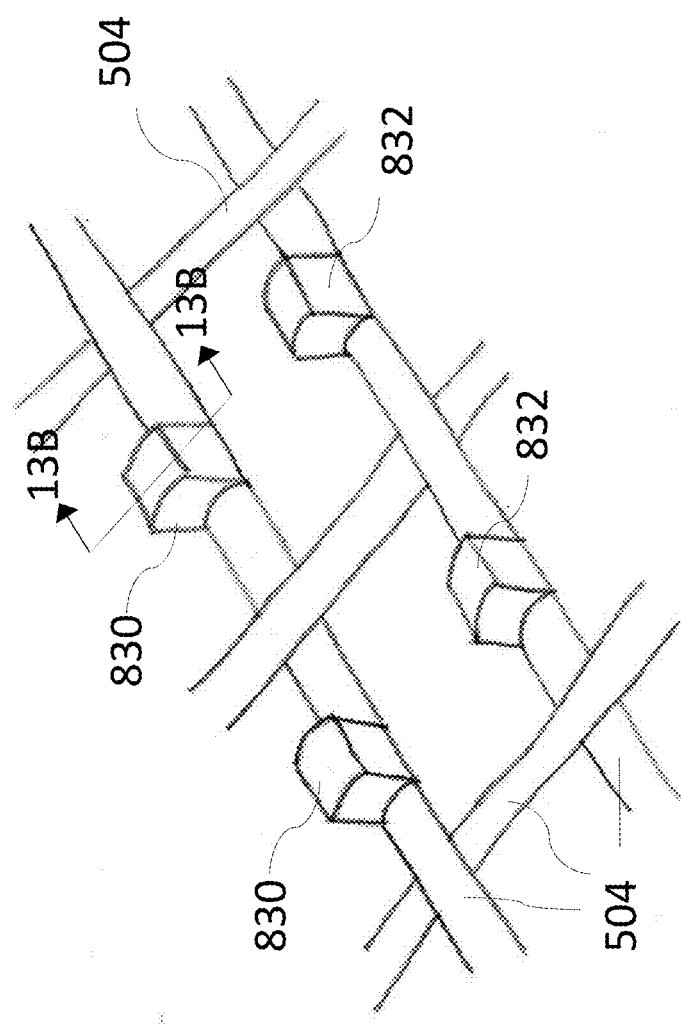
FIG. 13A is an expanded view of FIG. 12B showing an example of a tissue-integrating electrodes formed directly on the flexible wires of a scaffold. For clarity, the polymeric coating is omitted from the scaffold, according to an embodiment.

An expanded view of a portion of the electrochemical apparatus shown in FIG. 12B is illustrated in FIG. 13A. As illustrated in FIG. 13A, at least one tissue-integrating electrode (e.g. at least one working electrode 830 and at least one reference/counter electrode 832) is formed as a discrete patch on one or more flexible wires 504. The flexible wire 504 serves as a conductive layer 806 onto which one or more other layers are coated. In an embodiment, each tissue-integrating electrode may also include one or more of an inner selective membrane layer 808, an enzyme layer 810 and an outer diffusion limiting membrane layer 812, as illustrated in FIG. 13B (cross-sectional view of a working electrode 830 shown in FIG. 13A).

Figure 14B:
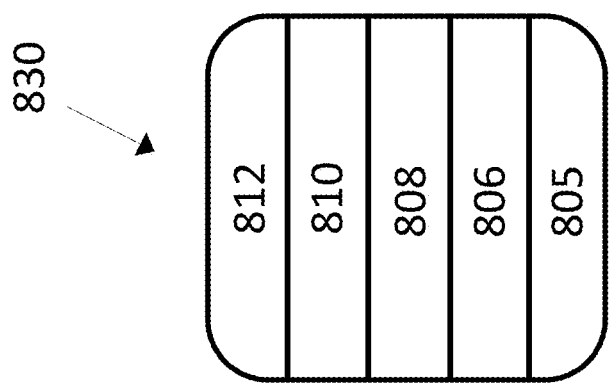
FIG. 14B is a cross-sectional view of an example of the electrode illustrated in FIG. 14A.
Figure 14A:
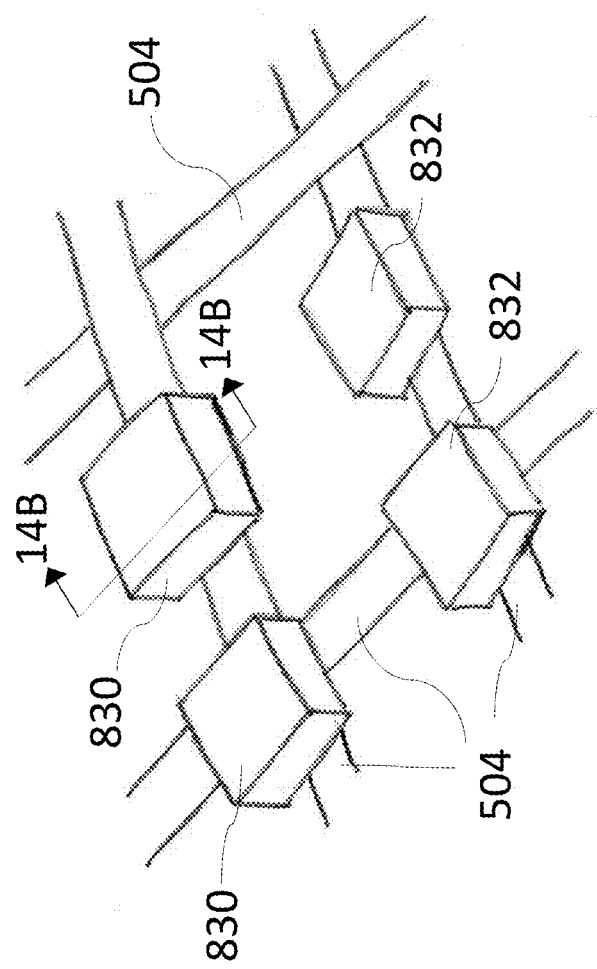
FIG. 14A is an expanded view of FIG. 12B showing examples of tissue-integrating electrodes formed on a substrate, which is mounted on a flexible wire of a scaffold, according to an embodiment. For clarity, the polymeric coating is omitted from the scaffold.

Another expanded view of a portion of the electrochemical apparatus shown in FIG. 12B is illustrated in FIG. 14A. As illustrated in FIG. 14A, the flexible wire 504 is used as a support for multiple electrodes and to connect the electrodes to a voltage source (e.g., a potentiostat). The electrodes can be formed in a separate process and are then mounted onto the scaffold. Each electrode may include a substrate 805 onto which the conductive layer 806, the inner selective membrane layer 808, the enzyme layer 810 and the outer diffusion limiting membrane layer 812 are disposed, as illustrated in FIG. 14B (cross-sectional view a working electrode 830 shown in FIG. 14A).

Processes used to form the layers directly on the flexible wire 504 include dip coating, spray-coating, vapor deposition, electro-deposition, etching and/or ink printing. Exemplary processes used to form the layers on the substrate 805 include spray-coating, vapor deposition, electro-deposition, etching and/or ink printing. In embodiments of the electrochemical sensor having a substrate 805, the substrate 805 may be formed from a planar sheet of material such as, but not limited to, polyimide and/or polyethylene tetraphthalate (PET).

The conductive layer 806 for forming electrodes may be used for the electrochemical measurement of an analyte (e.g., glucose). In an embodiment, one electrode is formed in the conductive layer 806. In another embodiment, more than one electrode (e.g., one or more working, reference and/or counter electrodes) may be formed in the conductive layer 806. The conductive layer 806 may also include one or more conductive tracks electrically coupled to one or more contact pads that connect each electrode to a voltage source by, for example, spot welding each contact pad to a flexible wire 504. Examples of materials from which the conductive layer 806 may be formed include Au, Pd, Pt, Ag, Cu, Al, Ni, Zn, carbon, iridium and/or titanium. In embodiments, the conductive layer 806 may be 100 nanometers or less in thickness.

The inner selective membrane layer 808 substantially restricts, resists, or blocks one or more interferents from reaching the electrochemically reactive surface of the electrochemical sensor. The interferents may be reduced or oxidized, resulting in a false positive analyte signal. Thus, the inner selective membrane layer 808 allows the analyte of interest to reach the electrode surface while being less permeable to the one or more interferents. In an embodiment in which the sensor detects glucose, typical interferents include acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid. Examples of materials from which the inner selective membrane layer 808 may be formed include cellulose acetate, cellulose acetate butyrate, 2-hydroxyethyl cellulose, cellulose acetate phthalate, cellulose acetate proprionate and/or cellulose acetate trimellitate. In embodiments, the inner selective membrane layer may have a thickness of about 0.05 microns to about 20 microns.

The enzyme layer 810 includes at least one enzyme to catalyze the reaction of the analyte and the enzyme cofactor. In an embodiment in which glucose is the analyte of interest, glucose oxidase is included in the enzyme layer 810. In other embodiments, pyruvate oxidase, alcohol dehydrogenase, lactate dehydrogenase, lactate oxidase, ethanol oxidase, pyruvate oxidase, bilirubin oxidase, histamine oxidase, glucose dehydrogenase or any combination of oxidases and/or dehydrogenases may be included in the enzyme layer. Other additives necessary to functional operation of the sensor may also be included in the enzyme layer including, but not limited to, buffer for maintaining a pH, cofactors and oxygen enhancing substances such as silicone or fluorocarbon. In embodiments, the enzyme layer may have a thickness of about 0.05 microns to about 20 microns.

The outer diffusion limiting membrane layer 812 controls the flux of oxygen and analyte to the enzyme layer such that oxygen is in non-rate-limiting excess. Inclusion of the outer diffusion limiting membrane layer 812 extends the upper limit of the linear range of the analyte measurement. In embodiments, the outer diffusion limiting membrane layer 812 may be formed from silicone polymer and/or hydrophobic-hydrophilic polymer blends including, but not limited to, components such as polyvinylpyrrolidone (PVP), polyhydroxyethyl methacrylate, polyvinyl alcohol, polyacrylic acid, polyethers such as polyethylene glycol or polypropylene oxide, and copolymers thereof, including, for example, di-block, tri-block, alternating, random, comb, star, dendritic, and graft copolymers. In embodiments, the outer diffusion limiting membrane layer 812 may have a thickness of about 0.05 microns to about 20 microns.

The one or more tissue-integrating electrodes may be electrically connected in series or in parallel to a voltage source in an implantable module 518 by one or more flexible wires 504, as will be described with reference to FIG. 17.

It will be apparent that the overall dimensions of the implantable electronic apparatuses 500-800 will vary according to the subject and/or the analyte(s) or properties to be measured. Typically, the implant will be between about 0.001 mm to 2 mm in thickness (or any value there between) and between 1 mm and 1 cm in diameter (or an equivalent cross sectional area of a non-circular shape, for example length/width) and 15 mm in length or less, for example a disk shaped sensor that is 2 mm or less thick and 10 mm or less in diameter. In certain embodiments, the approximate sensor size in injectable form is approximately 100-1000 microns in diameter and the length is between 0.25 mm and 10 mm. The size of the tissue-integrating sensing media in disk form is typically 2 mm or less thick and 10 mm or less in diameter.

The electronic apparatuses 500-900 may be any suitable form including, but not limited to block-like (or any thickness), cube-like, disk-shaped, cylindrical, oval, round, random or non-random configurations of fibers and the like.

The injected apparatus may be a single piece of tissue-integrating material, or it may be several pieces or particles of tissue-integrating sensing material. The apparatus may be injected with a carrier substance (e.g. saline, PBS with anti-inflammatory drugs or other tissue-response modifiers). Furthermore, the apparatus may be implanted into any part of the subject, including, for example, shoulder, arm, leg, abdomen, etc. The apparatus may be implanted into the skin, for example, the epidermis, the dermis and/or the subcutaneous layer of skin. The apparatus may also be implanted into muscle and/or organs.

Methods of Making Tissue Integrating Apparatuses

Some embodiments include a method for making tissue-integrating electronic apparatuses. The method for forming tissue-integrating electronic apparatuses comprises a process for combining the scaffold 502 and the other elements of the sensor in a manner that preserves the integrity of the signal (e.g., optical or electrochemical) measured in response to the analyte of interest.

In some embodiments, the methods of the invention involve a tissue-integrating electronic apparatus that has a scaffold formed by combining flexible wires having integrated electronic components (e.g., one or more LEDs, detectors, electrodes, temperature sensors, accelerometers and/or pressure sensors) with polymeric material. For tissue-integrating opto-electronic apparatuses, sensing moieties are embedded or contained within the polymeric material of the tissue-integrating scaffold 502. For tissue-integrating electrochemical apparatuses, sensing moieties are typically not included in the polymeric material of the scaffold.

Figure 15:
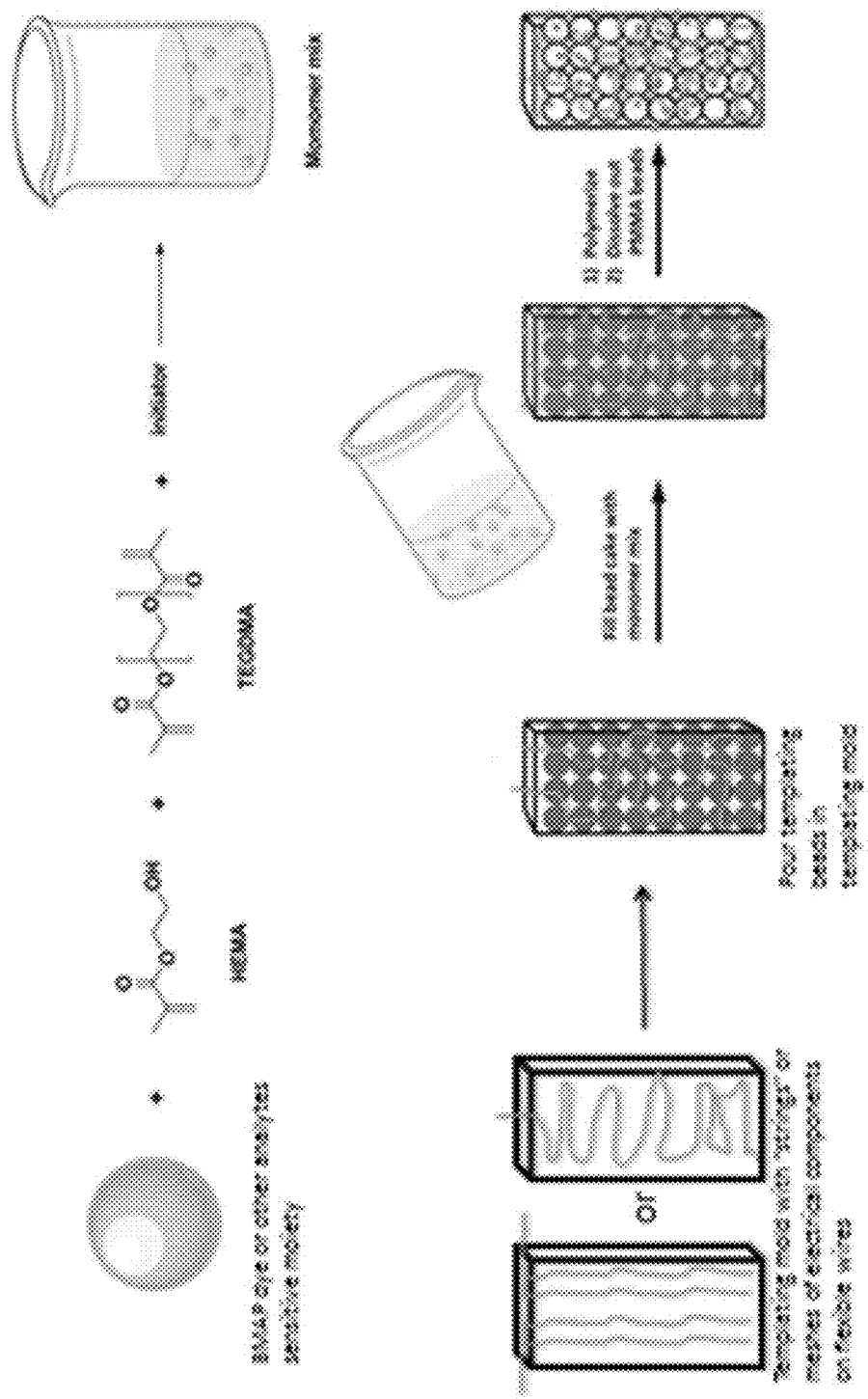
FIG. 15 is a flow chart of a process for manufacturing a tissue-integrating electronic apparatus in which a templating mold is used, according to an embodiment.

Referring to FIG. 15, the process of manufacturing a tissue-integrating electronic apparatus may begin with combining strings or meshes of flexible wires having integrated electronic components with a polymer precursor (e.g. monomer, polymer beads, etc.), followed by the formation of the scaffold (e.g. polymerization around template beads, multiphoton polymerization, electro spinning, micro- and nano-printing fabrication techniques, polymer foaming, salt leaching, etc.) and the removal of any residuals (e.g. dissolution of template beads, removal of unpolymerized monomers, etc.). In an embodiment in which a tissue-integrating opto-electronic apparatus is formed, sensing moieties may be included in the step at which the flexible wires are combined with the polymer precursor. In an embodiment in which a tissue-integrating electrochemical sensor is formed, sensing moieties may be omitted in the step at which the flexible wires are combined with the polymer precursor.

Figure 16:
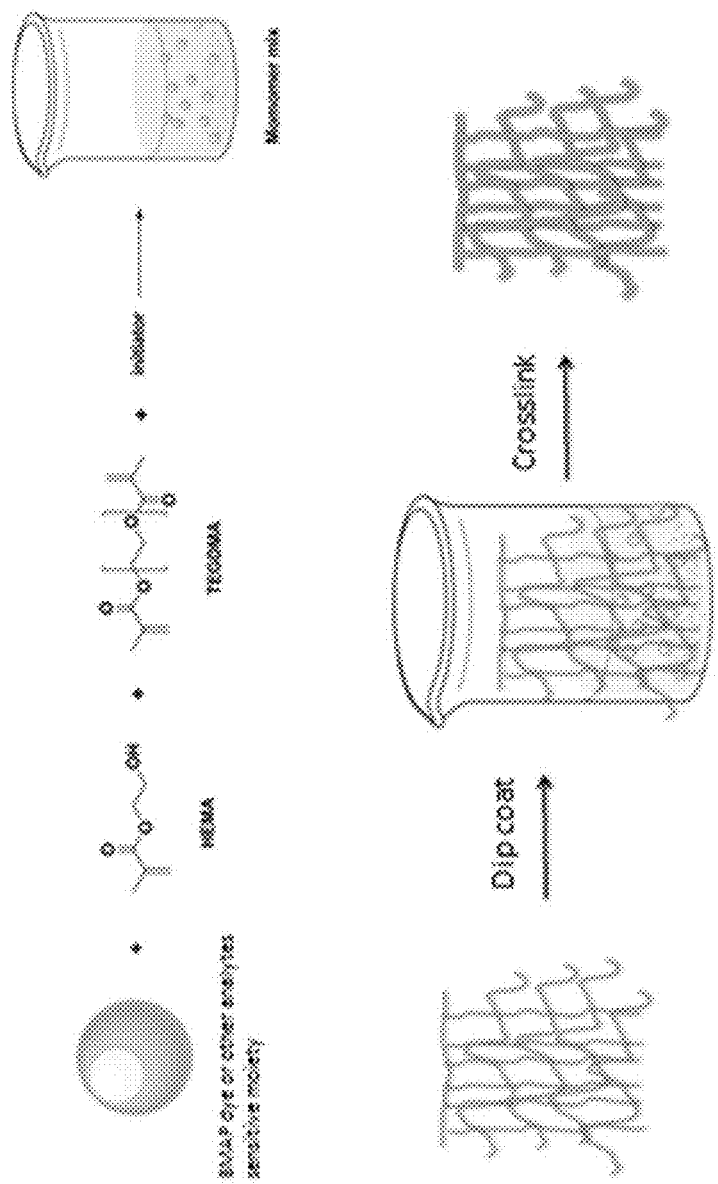
FIG. 16 is a flow chart of a process for manufacturing a tissue-integrating electronic apparatus in which dip coating is used, according to an embodiment.

Referring to FIG. 16, in other embodiments, the process of manufacturing a tissue-integrating electronic apparatus may begin with dipping or coating e-fabric or meshes of flexible wires having integrated electronic components in a polymer precursor (e.g. monomer) with or without sensing moieties, followed by crosslinking of the polymeric material and removal of any unpolymerized monomers.

In embodiments having sensing moieties, it will be apparent that the relative amounts of polymeric material, sensing moieties and/or reference moieties in the apparatuses will depend on the polymers and sensing moieties used. For example, in certain embodiments, the sensor will be made with between about 2-95% vol/vol of a monomer or polymer (e.g., 2-85% vol/vol HEMA). Likewise, when present, the amount of cross-linker used will depend on the polymer, for example typically about 0.1 and 10% vol/vol of TEGDMA may be used. Water and or other solvents may be present in any amount (e.g., 5-95% vol/vol water or polyethylene glycol). Initiators may also present in any amount, for example 0.35 to 5% vol/vol of Irgacure. Sensing moieties may be present in any suitable amount, for example, oxygen sensing porphyrins (PdP) may be included at a concentration of about 200 nM to 1 nM.

In embodiments having sensing moieties, non-limiting exemplary methods for embedding or containing the sensing moieties within the polymeric material of the tissue-integrating scaffold include (but are not limited to): polymerization around template beads with or without subsequent dissolution, matrix or other structure, polymerization of a three-dimensional structure using multiphoton polymerization or 3D printing, electrospinning of small fibers, sintering or melting scaffold precursor structures, or swelling the polymeric material to permit entry of sensing moieties followed by shrinking of scaffold. In certain embodiments, the method comprises polymerizing glucose sensing moieties (nanospheres) into an inverted crystal colloid (ICC) polymeric material.

In other embodiments having sensing moieties, the sensing moieties are immobilized (conjugated or physically entrapped) on (or to) the surface of the tissue-integrating scaffold. The process begins with an existing scaffold or the forming of a scaffold, followed by the attachment of the sensing moieties to the scaffold. The method may also include a coating step that protects or holds in place (e.g. physical entrapment) the sensing moieties to the scaffold. The coating may have the added benefit(s) of (1) protecting the surface chemistry from degradation (e.g. proteases); (2) a diffusion barrier (surface fouling); (3) improving the biocompatibility (e.g. PEG, chitosan, pHEMA, etc.); (4) altering or improving the surface characteristics (e.g. smoothness, pore size, hydrophilicity, etc.). Exemplary methods for immobilizing the sensing moieties on the tissue-integrating scaffold include, but are not limited to: conjugation chemistry, adsorption, electrostatics and covering with a continuous coating. Exemplary coatings include PEG, pHEMA and chitosan.

In some embodiments, the apparatus is formed by constructing simple or multi-layer fiber(s) implants. The polymeric material (with or without sensing moieties) is part of one or more of the base materials from which the fiber scaffold is created or the polymeric material is contained in or comprises one of the layers of sequential building up of layers. Some example processes for producing such multi-layer fibers and/or for creating the layers of polymeric material on top of already formed fibers are extrusion, electrospinning, dip coating, spray forming, printing, stamping, rolling, multiphoton polymerization and plasma deposition.

In some embodiments, the apparatus is formed by 3D printing of conductive or non-conductive polymer in sequential layers along with flexible wires to form an electronic apparatus of the desired shape and size. In these embodiments, one or more sensors may be placed in one or more layers of the apparatus manually or automatically by a pick-and-place (or robotic) machine.

In forming any of the apparatuses as described herein, the methods may also include step(s) for the sterilization of the apparatus prior to implantation (e.g. ethylene oxide gas) or in vitro use.

Tissue Integrating Electronic Systems

Referring to FIGS. 17-20B, systems for detecting one or more analytes are illustrated according to exemplary embodiments of the invention. In an embodiment, the system is used to continuously or semi-continuously detect at least one analyte concentration from an in vivo sample (e.g., tissue). The system may, for example, be implanted subcutaneously at a depth of about 1 to 5 mm below the surface of the skin.

The systems 1000-1300 include one or more tissue-integrating apparatuses operably connected to the implantable (tissue integrating or tissue anchoring) module 518 by the one or more flexible wires 504. The wires may be bonded to the implantable module 518 by, for example, a wire bonding process using heat, pressure, ultrasonic energy, metal deposition in a vacuum, ink jet type printing, and/or micro-plasma printing. As shown in FIG. 17, the flexible wires 504 may be coated with polymeric material 506. The systems 1000-1300 may further include an external device 520.

The implantable module 518 includes a power source 522 that powers the sensor and control circuitry 524 (e.g., an application-specific integrated circuit or ASIC) that controls the electronic components of the one or more sensors. In embodiments, the power source 522 includes a battery, inductor, a photovoltaic cell, or the like, as is appreciated by one skilled in the art. In embodiments having tissue-integrating electrochemical apparatuses 700 and/or 800, in addition to the power source 522, the implantable module 518 includes a potentiostat that is operably connected to and applies one or more test voltages to the one or more tissue-integrating electrodes such that one or more electrical signals (e.g., test current or voltage) may be measured from the sensor.

The implantable module 518 may also include a power storage component, a signal processor, a signal transmitter, a data transmitter and/or a data processor.

The implantable module 518 may include one or more components or features that are tissue integrating and/or tissue anchoring. In embodiments, the power source 522 and control circuitry 524 are formed on a substrate 526 (e.g., a printed circuit board). The substrate 526 may be tissue anchoring and may include a plurality of perforations 528 or holes to promote collagen and/or tissue in-growth. The substrate 526 or may be partially (see FIG. 18A) or completely covered in the plurality of perforations. The plurality of perforations 528 typically are at least 1 micron in one dimension. The plurality of perforations may be formed in the substrate 526 during manufacture of the substrate (e.g., through photolithography) or may be added to the substrate after manufacture by using a laser to punch holes in the substrate. In certain embodiments, the tissue anchoring substrate 526 includes a porous coating of polymeric material 506 as described previously. In other embodiments, the tissue anchoring substrate 526 includes a textured coating or surface as described previously.

Exemplary substrate materials include polyester (e.g., Mylar), plastic, fiberglass, polyimide, PEEK, transparent conductive polyester, or combinations thereof. Exemplary processes for forming the substrate include photolithography, silk screening, milling, ink jet printing and/or various 3-D printing technologies.

The external device 520 may include a signal receiver, a signal transmitter, a signal processor, a power source, a data processor, a memory for storing data and/or an optional display for displaying data. In an embodiment in which a tissue-integrating opto-electronic apparatus includes one or more light sources and no detector, the external device 520 may also include one or more detectors. The external device 520 may be a wearable patch that resides over the sensor to detect the signal or may be a hand held or other device that is periodically held over the implanted sensor to take the measurement.

Referring to FIGS. 17-20B, in operation of a system having a tissue-integrating opto-electronic apparatus, the one or more light sources 508 are activated to transmit light to the sensing moieties 514 within the apparatus. The sensing moieties 514 absorb light from the light sources 508 and emit light (e.g., fluorescent light) in a manner dependent on the concentration of the analyte of interest. The emitted light is detected by the one or more detectors 510 located in the apparatus or in the external device 520. The light detected by the one or more detectors 510 is then converted into a digitized signal that is processed by a microprocessor located in the implantable module 518 or in the external device 520. The digitized signal may be stored in memory and/or be used to calculate an analyte concentration, which may then be displayed on a display in the external device 520. The analyte concentration may optionally be wirelessly transmitted to and displayed on a remote device such as a cell phone, a smart phone, a smart watch, a personal data assistant and/or a computer.

Referring to FIG. 17, in operation of a system having a tissue-integrating electrochemical sensor 800 or 900, one or more test voltages are applied to the one or more electrodes in the sensor 800/900. Current is generated at the one or more electrodes in a manner dependent on the concentration of the analyte of interest. The generated current is converted into a digitized signal that is processed by a microprocessor located in the implantable module 518 or in the external device 520. The digitized signal may be stored in memory and/or be used to calculate an analyte concentration, which may then be displayed on a display in the external device 520. The analyte concentration may optionally be wirelessly transmitted to and displayed on a remote device such as a cell phone, a smart phone, a smart watch, a personal data assistant and/or a computer.

EXAMPLES

The following examples serve to illustrate, but not to limit, the present invention.

Example 1

Skin Preparation
Sensing Media Insertion
Post-Healing Patch
Sensor Maintenance Patch Assembly
Explant Patch A 0.75 cm×2 cm rectangular skin preparation patch containing 300-750 µg of betamethasone, 3.5 mg/gm neomycin base, 10,000 polymyxin B units/gm, and 0.5% hydrocortisone acetate 5 mg (0.5%) is placed on the skin over the site of implantation, where it adheres to the skin by an adhesive covering the bottom surface of the patch. The drugs are contained in a section of the adhesive, and drug diffuses during the next 12-24 hours through the skin. The skin preparation patch also has a 1- to 2-mm hole near one edge that is used to guide the implantation process. The analyte sensing media, such as a 0.5 mm×10 mm rod-shaped pHEMA hydrogel implant containing analyte sensing chemicals, such as concanavalin A and dextran, or a phenylboronic-derivatized hydrogel backbone, or other reversible ligand-binding analyte pair, is inserted by syringe using the guide hole into the dermis or subcutis 0.5-5.0 mm below the surface. The skin preparation patch is removed, and the skin is cleansed. A 1.5- to 3-cm circular topical drug post-insertion healing patch containing 25 mg of 1% wt/vol of sildenafil or other nitric oxide synthase inhibitor, 10 mg of 2.5%-25% of L-arginine, and/or 2.5 mg of estradiol, is placed on the skin over the site of implantation, where it adheres to the skin by an adhesive covering the bottom surface of the patch. These drugs or agents may be contained in the entire surface adhesive, in a section of the adhesive, or in a mechanical depot within the patch with manifold orifices over the prescribed surface above the implant, and the drugs diffuse through the skin to achieve an effective local concentration to encourage controlled neovascularization, vascular permeability, and control of overactivity of macrophages during implant tissue ingrowth and healing. The patch remains in place for 24-48 hours, and is then removed. A sensor maintenance patch assembly, comprising a drug delivery interface and an electronic signal interrogation component (e.g., light-emitting diodes and filtered photodiodes for fluorescence), is placed over the site of the implant. The drug delivery component provides, for example, an adhesive for adhering the patch to the skin. The drug delivery component contains 125 mg of 65- to 100-mM mannose-6-phosphate or 5% wt/wt halofuginone, and 100 mg of 2.5%-25% L-arginine, to inhibit collagen capsule formation and to maintain adequate blood vessel dilation, respectively. This patch is left on the skin for 5-15 days, and during this time the interrogator collects data from the implant. After 5-15 days, the patch is removed and the two components are separated. The drug delivery component is discarded, and a new drug delivery component is assembled to the electronic signal interrogation component, and the assembly is then placed over the implant site. Analyte sensing media interrogation then resumes. These steps may be repeated as long as necessary. At the end of the operational life of the implanted analyte sensing media, an explantation preparation patch containing 50-150 mg of 0.1% dexamethasone is placed over the analyte sensing media implant site and allowed to stay in place for 3 days. The patch is then removed, and the analyte sensing media is safely explanted.

Example 2

Skin Preparation
Sensing Media Insertion
Sensor Maintenance Patch

A skin preparation patch is placed on the skin at the future implant site 6-24 hours before implantation of an implantable analyte sensor (e.g., glucose, lactate, pyruvate, glycerol, urea). The skin preparatory patch contains 50-150 mg of 0.1% dexamethasone, which is released at a rate sufficient to achieve localized concentrations of 0.05-20.0 mg/kg in an area ranging from 0.5 cm to 4.0 cm in diameter and 0.05 cm to 1.0 cm in depth. The patch also contains a temporary skin colorant, e.g., 2-hydroxy-1,4-naphthoquinone (also called Henna), which will diffuse into the skin to demarcate the area that has been directly exposed to the dexamethasone. Alternatively, a wide selection of temporary transfer tattoo inks may be utilized as the temporary colorant in the skin preparatory patch. Yet another alternative for use as the temporary skin colorant is providone iodine (Betadine®), which can also sterilize the skin in preparation for injection, incision or other planned perforations of the skin barrier. Yet another alternative skin colorant to denote the implant area is a substance that will be visible only under UV light, such as sodium fluorescein, which is widely used and considered safe for epi-cutaneous labeling. After 2-24 hours, the skin preparation patch is removed, and the analyte sensor is implanted. Alternatively, implantation may take place prior to removing the pre-implant patch, thus avoiding the need for colorant, or the individual applying the patch may mark the skin with a marking pen or other implement before placing the patch.

The analyte sensing media is implanted via a syringe-like injection system at a depth under the outer surface of the skin ranging from 0.05 to 1.0 cm. The skin colorant, which was delivered by the skin preparatory patch and which remains visible on the skin under normal or UV light, is used as a visual guide to placement of the implant. The area of sensing media implantation coincides with the colorant demarcating the area of the skin that received the dexamethasone, which was delivered from the skin preparation patch.

Immediately after sensing media insertion, a second patch, called a post-insertion healing patch, is applied above the implant that delivers 0.01-3% diclofenac sodium, 3.5 mg/gm neomycin base, 10,000 polymyxin B units/gm, and 0.5% hydrocortisone acetate 5 mg (0.5%). The post-insertion healing patch releases contents in an area ranging from 0.5 cm to 4.0 cm in diameter and to a depth ranging from 0.05 cm to 1.0 cm. The post-insertion healing patch is left in place for 3 to 7 days, after which time it is removed.

After the removal of the post-insertion healing patch, the surface of the skin in the area of the analyte sensing media is washed with mild detergent to remove surface oils and rinsed thoroughly with water. The area is swabbed with rubbing alcohol and allowed to air-dry. A third patch type, the sensor maintenance patch, is then applied to the surface of the skin over the analyte sensing media site. The sensor maintenance patch contains 5% wt/wt halofuginone or 125 mg of 65- to 100-mM mannose-6-phosphate to inhibit collagen synthesis and prevent collagen capsule formation within or around the analyte sensing media. The sensor maintenance patch also contains electronics for optical interrogation of the sensor and radio frequency communication. Upon placement of the sensor maintenance patch, the patient conducts a 2 point capillary blood glucose calibration, and begins taking readings. Every 7 days, a patch replacement procedure is conducted. The old sensor maintenance patch is removed; the area is washed with a mild detergent, rinsed thoroughly with water, dried, swabbed with rubbing alcohol, and allowed to air-dry. A fresh replacement sensor maintenance patch is then applied over the implant, and a capillary blood glucose calibration is conducted. Collection of analyte measurements then resumes. The sensor maintenance patch replacement procedure is conducted every 7 days throughout the lifetime of the inserted sensor.

After the useful life of the analyte sensing media, the sensor maintenance patch is removed, and the area is washed, rinsed, and swabbed with disinfectant. The analyte sensing media is then removed via a minimal incision. To continue analyte measurements, a fresh analyte sensing media may be implanted in a different location following the above procedure (including application of a skin preparation patch). The new analyte sensing media may be implanted greater than 2 cm away from the first sensor. This entire procedure may be repeated as many times as needed to replace a sensor whose useful life has expired. Also, this entire procedure may be repeated as many times as needed for insertion of multiple analyte sensors.

Example 3

Analyte Sensing Media Insertion
Post-Implant Healing Patch
Sensor Maintenance Patch Analyte sensing media, such as a 0.5 mm×10 mm rod-shaped pHEMA hydrogel implant containing analyte sensing chemicals, such as concanavalin A and dextran, or a phenylboronic-derivatized hydrogel backbone, or other reversible ligand-binding analyte pair, is implanted into the dermis 0.5 mm to 5 mm below the surface of the skin by syringe or catheter. A 1.5- to 3-cm circular topical drug post-insertion healing patch containing 25 mg of 1% wt/vol of sildenafil or other nitric oxide synthase inhibitor, 10 mg of 2.5%-25% of L-arginine, and/or 2.5 mg of estradiol, is placed on the skin over the site of implantation, where it adheres to the skin by an adhesive covering the bottom surface of the patch. These drugs or agents may be contained in the entire surface adhesive, in a section of the adhesive, or in a mechanical depot within the patch with manifold orifices over the prescribed surface above the implant, and the drugs diffuse through the skin to achieve an effective local concentration to encourage controlled neovascularization, vascular permeability, and control of overactivity of macrophages during implant tissue ingrowth and healing. The patch remains in place for 24-48 hours, and is then removed.

After this period, a sensor maintenance patch comprising a drug delivery interface (e.g., cream, ointment, microneedles, iontophoretic electrode and drug reservoir) and an electronic signal interrogation interface (e.g., light-emitting diodes and filtered photodiodes for fluorescence) is placed over the site of the implant. The drug delivery component contains 100 mg of L-arginine, and 125 mg of 65- to 100-mM mannose-6-phosphate or 100 mg of 5% wt/wt halofuginone. The L-arginine maintains blood flow through the newly generated microvessels within the implant, and low-dose mannose-6-phosphate or halofuginone inhibit overabundant Type 1 collagen capsule formation, which would otherwise reduce diffusion of analyte to the sensor. This patch is left on the skin for 3-14 days, and during this time the interrogator collects data from the implant. After 3-15 days, the sensor maintenance patch is removed and discarded, and another sensor maintenance patch is placed over the implant site, and interrogation of the sensor implant continues. These latter steps may be repeated as long as necessary.

Example 4

Analyte Sensing Media Insertion
Post-Implant Healing
Interrogation Only
Explant Patch A 0.5 mm×10 mm rod-shaped hydrogel implant containing analyte sensing chemicals, such as concanavalin A and dextran, or phenylboronic derivatized hydrogel backbone, or other reversible ligand-binding analyte pair, is implanted into the dermis 2-3 mm below the surface by syringe or catheter. A post-insertion healing patch is applied above the implant that delivers 25 mg of 17B estradiol, 0.01-3% diclofenac sodium, an NSAID (non-steroidal anti-inflammatory drug), 3.5 mg/gm neomycin base, 10,000 polymyxin B units/gm, and 0.5% hydrocortisone acetate 5 mg (0.5%). The post-implant healing patch releases contents in an area ranging from 0.5 cm to 4.0 cm in diameter and a depth ranging from 0.05 cm to 1.0 cm. The post-implant healing patch is left in place for 3 to 7 days, after which time it is removed. After the removal of the post-insertion healing patch, the surface of the skin in the area of the implant is washed with mild detergent to remove surface oils and rinsed thoroughly with water.

After this healing period, an interrogation patch—comprising light-emitting diodes and filtered detector photodiodes, microprocessor, power source, and RF communication module, for fluorescence detection—is placed on the skin over the implant site and allowed to stay in place for 30-180 days. The interrogation patch may be held in place by an adhesive that is replenished every 5-15 days or by a strap or other means to hold the patch against the surface of the skin. During this time, data are continuously collected from the implant.

If an adhesive is used, after a period of 5-15 days, the interrogation patch is removed and the adhesive component is replaced with a fresh adhesive component, and the interrogation patch is placed back on the skin over the implant. This procedure may be repeated as often as necessary over the life of the implant.

When the implant reaches the end of its operational life, a cream or ointment containing 0.05% clobetasol 17-propionate is applied to the skin above the implant 2-3 times per day for 24-72 hours to prepare the tissue for explantation. This encourages devascularization of the implant. The implant is then removed.

Example 5

Skin Preparation
Analyte Sensing Media Insertion
Interrogation
Explant Patch

A skin preparation cream or ointment containing a mild to moderately potent steroid, e.g., 0.25% fluocinolone acetonide or 1% hydrocortisone acetate, is applied to a 1- to 4-cm diameter area of skin where an analyte sensing media will later be implanted. Application of the cream or ointment is repeated every 4-6 hours for at least 24 hours. The cream or ointment is removed and the analyte sensing media is placed into the dermis 0.5 mm to 10 mm below the surface of the skin. For the next 7-10 days the implant is allowed to heal in place. After this healing period, an interrogation patch—comprising light-emitting diodes and filtered detector photodiodes, microprocessor, power source, and RF communication module, for fluorescence detection—is placed on the skin over the implant site and allowed to stay in place for 30-180 days. The interrogation patch may be held in place by an adhesive that is replenished every 5-15 days or by a strap or other means to hold the patch against the surface of the skin. During this time, data are continuously collected from the implant. If an adhesive is used, after a period of 5-15 days, the interrogation patch is removed and the adhesive component is replaced with a fresh adhesive component, and the interrogation patch is placed back on the skin over the implant. This procedure may be repeated as often as necessary over the life of the implant.

When the implant reaches the end of its operational life, a cream or ointment containing 0.05% clobetasol 17-propionate is applied to the skin above the implant 2-3 times per day for 24-72 hours to prepare the tissue for explantation. This encourages devascularization of the implant. The implant is then removed.

Example 6

Skin Preparation
Analyte Sensing Media Insertion
Post-Insertion Healing
Sensor Maintenance Patch
Explant Patch A 0.75 cm×2 cm rectangular skin preparation patch containing 300-750 μg of betamethasone is placed on the skin over the site of implantation, where it adheres to the skin by an adhesive covering the bottom surface of the patch. The drug is contained in a section of the adhesive, and drug diffuses during the next 12-24 hours through the skin and achieves a dermal concentration of in the range of 0.1-1.0 μg/mL wt/vol in the tissue below. The formulation may contain a carrier and penetrant additive(s) to facilitate penetration. Betamethasone blocks certain aspects of the acute inflammation response in preparation for the implant to be placed into the tissue. The skin preparation patch also has a 1- to 2-mm hole near one edge that is used to guide the implantation process. The analyte sensing media is then placed via a syringe or catheter through the guide hole into the dermis or subcutis 0.5-5.0 mm below the surface. The skin preparation patch is then removed. A second patch, a post-insertion healing patch, containing 25 mg of 17B estradiol to facilitate healing as well as a small amount of non-steroidal anti-inflammatory compound to dampen other aspects of the acute inflammatory response, is applied over the site of implantation. This skin preparation patch is left in place for 24 hours, and then it is removed. The implant is then allowed to heal in place for the next 7-10 days. During this time, tissue in-growth, neovascularization, and tissue modification occurs.

After the healing phase, a sensor maintenance patch, comprising a drug delivery interface (e.g., cream, ointment, microneedles, iontophoretic electrode and drug reservoir) and an electronic signal interrogation component (e.g., light-emitting diodes and filtered photodiodes for fluorescence), is placed over the site of the implant. The drug delivery component provides an adhesive for adhering the patch to the skin. The drug delivery component contains 125 mg of 65- to 100-mM mannose-6-phosphate or 5% wt/wt halofuginone, and 100 mg of 2.5%-25% L-arginine, to inhibit collagen capsule formation and to maintain adequate blood vessel dilation, respectively. This patch is left on the skin for 5-15 days, and during this time the interrogator collects data from the implant.

After 5-15 days, the patch is removed and the two components are separated. The drug delivery component is discarded, and a new drug delivery component is assembled to the electronic signal interrogation component, and the assembly is then placed over the implant site. Analyte sensing media interrogation then resumes. These steps may be repeated as long as necessary.

At the end of the operational life of the implanted analyte sensing media, an explantation preparation patch containing 50-150 mg of 0.1% dexamethasone is placed over the analyte sensing media implant site and allowed to stay in place for 3 days. The patch is then removed and the analyte sensing media is safely explanted.

Example 7

Skin Preparation
Insertion
Light Treatment
Interrogation/Maintenance
Explant Patch A skin preparation cream or ointment containing 0.05% betamethasone or 1% hydrocortisone acetate is applied to a 1- to 4-cm diameter area of skin where an analyte sensor will later be implanted. The application is repeated every 6 hours for 24-48 hours. Then the analyte sensing media, such as described in other examples above, is then implanted into the dermis 0.5-5 mm below the surface by syringe or catheter. An adhesive band containing light emitting diodes or lasers to provide localized phototherapy is then applied to the skin after implantation over the area of implantation. The patch containing a cluster of 6 to 48 LED photons at 510-543, 594-599, 626-639, 640-670 842-872, and 1049-1082 nm wavelengths with 50-500 mW output power, is placed over the implantation area. 2-15 J/cm$^2$ treatments are administered 1-3 times daily to reduce inflammation and reduce damaging reactive oxygen species in the wound healing environment. Alternatively, a non-coherent light at 890 nm may be applied, which directs macrophages to send inhibitory signals to quiet fibroblast activity. Alternatively, or additionally, a light source at 625-635 nm may be used that inhibits cyclooxygenase (COX) and prostaglandin E(2) (PGE(2)), to reduce reactive oxidative species, and promote diabetic wound healing. Inhibition of COX and (PGE(2)) protects cells against cell injury in specific pathophysiological situations: inflammation and oxidative stress. Alternatively or additionally, a light source at 1072 nm light may be used, which has been shown to upregulate production of cytoprotective species (e.g., indicible nitric oxide synthase). Specified phototherapy depends on the stage of wound healing and foreign body response (e.g., initially anti-inflammatory 625-635 nm light may be used, and later, as the foreign body reaction ensues, 890 nm light to calm fibroblast activity and 1072 nm light to enhance NO production may be utilized). This treatment facilitates healing of the implant in the implant site and proceeds for 48-72 hours.

After treatment, a sensor maintenance patch containing 5% wt/wt halofuginone or 125 mg of 65- to 100-mM mannose-6-phosphate is placed to inhibit collagen synthesis and prevent collagen capsule formation within or around the analyte sensing media. The sensor maintenance patch also contains electronics for optical interrogation of the sensor and radio frequency communication. After this period, a second patch, comprising a drug delivery interface (e.g., cream, ointment, microneedles, iontophoretic electrode and drug reservoir) and an electronic signal interrogation interface (e.g., light-emitting diodes and filtered photodiodes for fluorescence), is placed over the site of the implant. The drug delivery component contains 100 mg of L-arginine, and 125 mg of 65- to 100-mM mannose-6-phosphate or halofuginone. The L-arginine maintains blood flow through the newly generated microvessels within the implant, and low-dose mannose-6-phosphate or halofuginone inhibit overabundant collagen capsule formation for optimal analyte diffusion. This patch is left on the skin for 3-14 days, and during this time the interrogator collects data from the implant.

After 5-15 days, the patch is removed and discarded, and another interrogation/drug patch is placed over the implant site, and interrogation of the sensor implant continues. These latter steps may be repeated as long as necessary.

The same patch described above with multiple wavelength LED clusters may be controlled via an external device (cell phone, hand-held, wristwatch, computer or other device) to activate certain LEDs and turn off others in order to change delivery wavelengths and/or intensity of phototherapy.

Example 8

Insertion
Healing Phototherapy
Interrogation Plus Maintenance Therapy

An electrochemical glucose sensor is implanted subcutaneously. For 1-3 weeks following implantation, tissue response modifiers in the form of specific wavelengths and intensity of light are delivered 1-3 times daily for 0.5-3.0 minutes from a portable hand-held device. This device is similar to a miniaturized version of the Biolux Research light emitting diode phototherapy device. Treatment is administered by the patient, who holds the light emitting portion of the device against the skin in the area of the implant for 0.5-3.0 minutes a day at an energy density of 1-50 mW/cm$^2$. The total dosage to the surface of the skin overlying the implant is 6-20 J/cm$^2$. This phototherapy regimen accelerates healing and improves angiogenesis. Optionally, silver oxide cream is applied twice daily to the implant area to enhance wound healing. After 1-3 weeks of localized phototherapy and application of silver oxide cream, the sensor has sufficiently healed into the tissue, and analyte measurements are ready to be taken. A hand-held RFID (radio frequency identification) and wireless battery charging device is placed in contact with the skin over the implant (may be the same device from which phototherapy was delivered above). The implant sends a signal to the hand-held and its internal battery is recharged wirelessly.

Upon initial use and once a week thereafter, a calibration procedure is performed that requires patients to measure capillary blood glucose using traditional fingerprick methods and enter that data into the hand-held device. The hand-held then converts the sensor signal to a glucose reading that is displayed to the patient. Any time the patient wishes to take a glucose reading, the hand-held device is held next to the skin.

Maintenance phototherapy may be delivered to the implant area 1-7 times a week for 0.5-10 minutes to insure the integrity of the tissue-sensor interface is maintained in a condition appropriate to generate sensor signals that reflect blood glucose readings. If continuous glucose monitoring is required rather than frequent checks that can be performed with the hand held (e.g., at night time for insulin dependent children), the patient may attached an RFID patch to the implant area, which will wirelessly transmit the signal coming from the electrochemical sensor to the hand-held device.

Example 9

Implant Drug Pump
Healing Patch

A fully implantable drug pump is implanted subcutaneously. Optionally, NSAID and utercalin microspheres are implanted adjacent to the pump outlet. A post-implantation healing patch, containing 25 mg of 17B estradiol, 0.01-3% diclofenac sodium, an NSAID, 3.5 mg/gm neomycin base, 10,000 polymyxin B units/gm, and 0.5% hydrocortisone acetate 5 mg (0.5%), is applied. This patch is left in place for 24 hours, and then it is removed. The patch-delivered drugs and the implanted microsphere-delivered drugs heal and condition the tissue around the pump outlet to prevent foreign body response occlusion of the outlet. The condition of the tissue around the pump outlet is maintained by replacing the patch with a maintenance patch containing 125 mg of 65- to 100-mM mannose-6-phosphate or 5% wt/wt halofuginone, and 100 mg of 2.5%-25% L-arginine. The maintenance patch may be replaced periodically.

Example 10

Production of a Tissue Integrating Opto-Electronic Apparatus

Electronic components (LEDs, photodiodes, a temperature sensor and a pressure sensor) are wire bonded to a flexible wire mesh using a conventional ultrasonic wire bonding process. The mesh containing electrical components is placed in a templating mold (two glass slides with Teflon spacers) into which sieved PMMA microspheres (36 microns with a CV less than 5%) are added. The template is sonicated for 10 minutes to closely pack the microspheres and then the template is heated to 177° C. for 24 hours to fuse the microspheres.

Polymer pre-cursor that will form part of the scaffold is then prepared. The general preparation of poly(2-hydroxyethyl methacrylate) (pHEMA) scaffold is as follows: In separate vials, two solutions are prepared: 0.89 ml of a 20% solution of APS (ammonium persulfate) in water and 0.3 ml of a 15% solution TEMED (tetramethylethylenediamine) in water. To a third vial 9.26 ml of HEMA (2-hydroxyethyl methacrylate), 4.6 ml of TEGDMA(triethyleneglycol-dimethacrylate), 2.6 ml of ethylene glycol and 2.68 ml of water are added by volume measurement and mixed.

The TEMED solution (vial 2) is added to the main pre-polymer (vial 3). Sensing nanospheres ranging from 2-95% volume of the total reactant volume (e.g. 5 ml of 100-200 nm alginate nanospheres containing fluorescent glucose sensing chemistry) are mixed with the pre-polymer solution (vial 3). The pre-polymer solution is filled into the mold and then the APS solution (vial 1) is added to the mold. The mold is placed under vacuum to remove any bubbles and completely infiltrate the PMMA-mold and then polymerized at room temperature for one hour. Next, the PMMA microspheres are dissolved by frequent exchange of dichloromethane or other solvent system for 24-48 hrs using a Soxhlet extractor or frequent volume changes. The resulting tissue integrating opto-electronic apparatus is connected to an implantable (tissue anchoring) electrical control circuit and power supply.

Example 11

Production of a Tissue Integrating Electrochemical Apparatus

A layer of gold is sputter coated onto a PET substrate at a thickness of about 20 nanometers to about 80 nanometers. Using photolithography, a plurality of electrodes, conductive traces and electrode contact pads are created by insulatively etching the gold. The electrodes will become the working and reference/counter electrodes of the apparatus. Using standard thin film techniques, the following layers are applied to the working and/or reference/counter electrodes: (1) an inner selective membrane layer of cellulose acetate at a thickness of about 20 microns or less; (2) an enzyme layer of glucose oxidase at an enzyme limiting amount and at a thickness of about 20 microns or less. The enzyme layer also includes a buffer for maintaining a pH and oxygen enhancing substances such as silicone or fluorocarbon; and (3) an outer diffusion limiting membrane layer of polyhydroxyethyl methacrylate and at a thickness of about 20 microns or less.

The resulting electrodes are singulated and the electrode contacts are wire bonded to wires in a flexible wire mesh. Electronic components (a temperature sensor and a pressure sensor) are also wire bonded to the flexible wire mesh. The wire mesh with electrodes and electronic components is placed in a templating mold into which sieved PMMA microspheres (36 microns with a CV less than 5%) are added. The template is sonicated for 10 minutes to closely pack the microspheres and then the template is heated to 177° C. for 24 hours to fuse the microspheres.

Polymer pre-cursor that will form part of the scaffold is then prepared. In separate vials, two solutions are prepared: 0.89 ml of a 20% solution of APS (ammonium persulfate) in water and 0.3 ml of a 15% solution TEMED (tetramethylethylenediamine) in water. To a third vial 9.26 ml of HEMA (2-hydroxyethyl methacrylate), 4.6 ml of TEGDMA(triethyleneglycol-dimethacrylate), 2.6 ml of ethylene glycol and 2.68 ml of water are added by volume measurement and mixed.

The TEMED solution (vial 2) is added to the main pre-polymer (vial 3). The pre-polymer solution is filled into the mold and then the APS solution (vial 1) is added to the mold. The mold is placed under vacuum to remove any bubbles and completely infiltrate the PMMA-mold and then polymerized at room temperature for one hour. Next, the PMMA microspheres are dissolved by frequent exchange of dichloromethane or other solvent system for 24-48 hrs using a Soxhlet extractor or frequent volume changes. The resulting tissue-integrating electrochemical apparatus may be connected to an implantable electrical control circuit having a potentiostat and a power supply.

Example 12

Production of an Implantable Electrical Control Circuit and Power Supply

An implantable electrical control circuit and power supply is fabricated on a tissue anchoring substrate. To create the tissue anchoring substrate, a plurality of holes ranging in size from 1 micron to 1000 microns are punched into a substrate such that the holes cover the entire substrate. The implantable electrical control circuit (/-a potentiostat) and power supply are fabricated onto the tissue anchoring substrate using standard photolithography techniques. One or more wires from electrical components of a tissue integrating opto-electronic apparatus or a tissue integrating electrochemical apparatus are bonded to wires from the implantable electrical control circuit and the power supply.

Example 13

Implantation

A system including a tissue integrating apparatus connected to an implantable electrical control circuit and power supply is placed in a 19-23 Gauge insertion needle, trocar, modified biopsy device or other devices engineered for injection under the skin.

Upon insertion, skin is pinched up so that the insertion needle is placed parallel to the surface of the skin 1-4 mm beneath the surface. Fluid or a reverse displacement plunger (or trocar) is used to leave the sensor in the tissue as the syringe is withdrawn. Insertion site may include any subcutaneous area, typically the abdomen, arm and thigh.

Example 14

Measurement

Data from a system having a tissue integrating electronic apparatus is collected, processed and displayed on a smart phone, other hand-held device, computer screen or other visualization format, for example using commercially available data display devices available for example from Medtronic. Raw data is converted to an analyte concentration or some non-quantitative representation of the analyte concentration (e.g. high, low, within range). Values at any given point in time or trends (graphs over time) or summary statistics over a period of time are provided. An indication of the quality of the data is optionally provided.

All patents, patent applications and publications mentioned herein are hereby incorporated by reference in their entirety.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, may be performed in reverse order when possible and may be performed sequentially as described above.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:
1. An apparatus, comprising:
a fabric, tissue-integrating scaffold;
a flexible wire woven through the fabric, tissue-integrating scaffold;
an analyte-sensing, tissue-integrating electrode coupled to the flexible wire; and
the flexible wire being configured to conduct at least one electrical signal flowing through the analyte-sensing, tissue-integrating electrode, the at least one electrical signal being associated with an amount of an analyte.
2. An apparatus, comprising:
a tissue-integrating scaffold;
an analyte-sensing, tissue-integrating electrode; and
a flexible wire embedded within the tissue-integrating scaffold and coupled to the analyte-sensing, tissue-integrating electrode, the flexible wire being configured to conduct at least one electrical signal flowing through the analyte-sensing, tissue-integrating electrode, the at least one electrical signal being associated with an amount of an analyte.

3. The apparatus of claim 2, wherein the analyte-sensing, tissue-integrating electrode is at least one of a working electrode or a counter electrode.

4. The apparatus of claim 2, wherein the analyte-sensing tissue-integrating electrode is one of a plurality of electrodes connected in series.

5. The apparatus of claim 2, wherein the analyte-sensing, tissue-integrating electrode is one of a plurality of electrodes connected in parallel.

6. The apparatus of claim 2, wherein the analyte-sensing, tissue-integrating electrode includes an enzyme layer including at least one of an oxidase or a dehydrogenase.

7. The apparatus of claim 2, wherein the analyte-sensing, tissue-integrating electrode includes an enzyme layer including at least one of glucose oxidase, lactate oxidase, pyruvate oxidase, ethanol oxidase, histamine oxidase or bilirubin oxidase.

8. The apparatus of claim 2, wherein the flexible wire is formed from at least one of Au, Pd, Pt, Ag, Cu, Al, aluminum alloys, Ni, Zn, Cr, Ti, W, doped amorphous or polycrystalline silicon, Mo, Ta, carbon, an aligned tissue or a conductive polymer.

9. The apparatus of claim 2, further comprising at least one of a temperature sensor, an accelerometer, a pressure sensor, a magnetic sensor or a piezoelectric sensor embedded within the tissue-integrating scaffold.

10. The apparatus of claim 2, wherein the tissue-integrating scaffold comprises a polymeric material.

11. The apparatus of claim 10, wherein the polymeric material comprises at least one of an insulating polymer or a conductive polymer.

12. The apparatus of claim 2, wherein the tissue-integrating scaffold comprises an e-fabric coated with a polymeric material.

13. The apparatus of claim 12, wherein the polymeric material comprises at least one of an insulating polymer or a conductive polymer.

14. The apparatus of claim 2, wherein the tissue-integrating scaffold is porous and at least two pores of the scaffold are interconnected.

15. The apparatus of claim 14, wherein the mean diameter of the at least two pores is between about 1 micrometers and about 100 micrometers.

16. The apparatus of claim 14, wherein the mean diameter of the pores is between about 10 micrometers and about 90 micrometers.

17. The apparatus of claim 14, wherein the mean diameter of the pores is about 30 micrometers.

18. The apparatus of claim 2, wherein the apparatus comprises two or more layers.

19. The apparatus of claim 2, wherein the tissue integrating scaffold comprises one or more fibers.

20. A method, comprising:
implanting an apparatus according to claim 2 into tissue of the subject; and
detecting the presence of the analyte.

21. The method of claim 20, wherein the tissue is a hypodermis, a subcutis, adipose fat, a dermis, a hypodermis, or a muscle.

22. A system, comprising:
an apparatus according to claim 2; and
a tissue-integrating module operably connected to the apparatus, the tissue-integrating module being configured to apply a test voltage to the analyte-sensing, tissue-integrating electrode and to measure an electrical signal flowing through the analyte-sensing, tissue-integrating electrode.

23. The system of claim 22, wherein the tissue-integrating module further comprises at least one of a power source, a voltage source, electrical control circuitry, a signal receiver, signal processor, a data transmitter or a data processor.

24. The system of claim 22, further comprising an external apparatus having at least one of a power source, a signal receiver, a signal processor, a data processor, memory for storing data or a display.

25. The system of claim 22, wherein the tissue-integrating module is operably connected to the apparatus by the flexible wire.

26. The apparatus of claim 2, wherein
the analyte-sensing, tissue-integrating electrode is embedded in the tissue-integrating scaffold, the analyte-sensing, tissue-integrating electrode having a substrate onto which is disposed at least one of an electrochemically conductive layer, an inner selective membrane layer, an enzyme layer or an outer diffusion limiting membrane; and
the flexible wire is electrically connected to the analyte-sensing, tissue-integrating electrode.

27. The apparatus of claim 26, wherein the tissue-integrating scaffold is a polymeric, tissue-integrating scaffold, the flexible wire embedded within the polymeric, tissue-integrating scaffold.

28. The apparatus of claim 2, wherein the tissue-integrating scaffold is a fabric, the flexible wire woven through the fabric.

29. The apparatus of claim 2, wherein the tissue-integrating scaffold is constructed entirely of a polymer.

30. The apparatus of claim 2, wherein the tissue-integrating scaffold is a sphere-templated hydrogel.

31. The apparatus of claim 2, wherein the tissue-integrating scaffold has a porosity suitable for capillaries to grow into the tissue-integrating scaffold.

32. The apparatus of claim 2, wherein the tissue-integrating scaffold defines a plurality of interconnected pores having a hallway pattern.

* * * * *